US012661335B2

(12) United States Patent
Kurosu et al.

(10) Patent No.: US 12,661,335 B2
(45) Date of Patent: Jun. 23, 2026

(54) HALOGENATED XANTHENE-CONTAINING TOPICAL ANTI-GRAM-POSITIVE BACTERIAL OPHTHALMIC COMPOSITION AND METHOD

(71) Applicants: Provectus Pharmatech, Inc., Knoxville, TN (US); University of Tennessee Research Foundation, Memphis, TN (US)

(72) Inventors: Michio Kurosu, Knoxville, TN (US); Dominic Rodrigues, Knoxville, TN (US); Edward V. Pershing, Knoxville, TN (US); Bruce Horowitz, Knoxville, TN (US); John Lacey, III, Knoxville, TN (US); Eric A. Wachter, Oak Ridge, TN (US); Edward P. Gamson, Highland Park, IL (US)

(73) Assignees: Provectus Pharmatech, Inc., Knoxville, TN (US); University of Tennessee Research Foundation, Memphis, TN (US)

( * ) Notice: Subject to any disclaimer, the term of this patent is extended or adjusted under 35 U.S.C. 154(b) by 168 days.

(21) Appl. No.: 18/089,134

(22) Filed: Dec. 27, 2022

(65) Prior Publication Data

US 2023/0270657 A1 Aug. 31, 2023

Related U.S. Application Data

(60) Provisional application No. 63/294,252, filed on Dec. 28, 2021.

(51) Int. Cl.

| | |
|---|---|
| ***A61K 8/81*** | (2006.01) |
| ***A61K 31/352*** | (2006.01) |
| ***A61N 5/06*** | (2006.01) |
| ***A61P 31/04*** | (2006.01) |
| ***C08F 220/58*** | (2006.01) |

(52) U.S. Cl.

CPC .......... *A61K 31/352* (2013.01); *A61K 8/8158* (2013.01); *A61N 5/062* (2013.01); *A61P 31/04* (2018.01); *C08F 220/585* (2020.02)

(58) Field of Classification Search

CPC ..... A61K 31/352; A61K 8/8158; A61P 31/04; C08F 220/585; A61N 5/062

See application file for complete search history.

(56) References Cited

U.S. PATENT DOCUMENTS

| | | | |
|---|---|---|---|
| 3,074,852 A | 1/1963 | Mayron | |
| 3,202,577 A | 8/1965 | Markus | |
| 3,330,729 A | 7/1967 | Johnson, Jr. | |
| 4,226,848 A | 10/1980 | Nagai et al. | |
| 4,615,697 A | 10/1986 | Robinson | |
| 5,221,722 A | 6/1993 | Shem | |
| 5,998,597 A | 12/1999 | Fisher et al. | |
| 6,331,286 B1 | 12/2001 | Dees et al. | |
| 6,493,570 B1 | 12/2002 | Dees et al. | |
| 6,991,776 B2 | 1/2006 | Dees et al. | |
| 7,229,737 B2 | 6/2007 | Fukushige et al. | |
| 7,390,668 B2 | 6/2008 | Dees et al. | |
| 7,402,299 B2 | 7/2008 | Dees et al. | |
| 7,648,695 B2 | 1/2010 | Dees et al. | |
| 7,863,047 B2 | 1/2011 | Dees et al. | |
| 8,470,296 B2 | 6/2013 | Dees et al. | |
| 8,530,675 B2 | 9/2013 | Singer et al. | |
| 8,557,298 B2 | 10/2013 | Scott et al. | |
| 8,974,363 B2 | 3/2015 | Dees et al. | |
| 9,273,022 B2 | 3/2016 | Singer et al. | |
| 9,422,260 B2 | 8/2016 | Singer et al. | |
| 11,331,257 B2 | 5/2022 | Piergallini et al. | |
| 2006/0194709 A1* | 8/2006 | Boone | C11D 17/0013 510/383 |
| 2008/0118578 A1* | 5/2008 | Dees | A61K 31/352 424/678 |
| 2014/0343296 A1 | 11/2014 | Singer et al. | |
| 2017/0224766 A1* | 8/2017 | Lim | A61K 9/1075 |
| 2019/0358142 A1 | 11/2019 | Piergallini et al. | |

OTHER PUBLICATIONS

International Preliminary Report on Patentability re International Application No. PCT/US2022/054076, dated Jun. 20, 2024.

Reiter, K.C. et al, "Inhibition of Biofilm Maturation by Linezolid in Meticillin-Resistant *Staphylococcus epidermidis* Clinical Isolates: Comparison with Other Drugs," Journal of Medical Microbiology, vol. 62, pp. 394-399, 2013. doi: 10.1099/jmm.0.048678-0.

Nsubuga, A. et al, "Investigating the Reactive Oxygen Species Production of Rose Bengal and Merocyanine 540-Loaded Radioluminescent Nanoparticles," Nanoscale Advances, vol. 3, pp. 1375-1381, 2021. doi: 10.1039/dona00964d.

Lambert, C.R. et al, "Electron Transfer Quenching of the Rose Bengal Triplet State," Photochemistry and Photobiology, vol. 66, No. 1, pp. 15-25, Jul. 1997. doi: 10.1111/j.1751-1097.1997.tb03133.x.

Nakonechny, F. et al, "Dark Antibacterial Activity of Rose Bengal," International Journal of Molecular Sciences, vol. 20, No. 13, pp. 3196, Jun. 2019. doi: 10.3390/ijms20133196.

(Continued)

*Primary Examiner* — Jianfeng Song
(74) *Attorney, Agent, or Firm* — Husch Blackwell LLP

(57) ABSTRACT

The present invention contemplates a topical ophthalmic system for treating a Gram-positive bacterially-infected mammalian eye. The system comprises an ophthalmic composition containing a halogenated fluorescein or a pharmaceutically acceptable salt or ester thereof dissolved or dispersed in an aqueous ophthalmic carrier and present in an anti-bacterial keratitis-treating effective concentration of about 0.2 μg/mL to about 50 μg/mL. The ophthalmic composition has a pH value of about 6.5 to about 7.6, a viscosity of about 10 to about 300 cps and an osmolality of about 270 mOsm/kg to about 340 mOsm/kg. The ophthalmic composition is present in a vessel opaque to actinic light. Also contemplated is a method of treating a mammal having a Gram-positive bacterial infection of an eye by administering the ophthalmic composition to the infected eye and maintaining the treated eye in the substantial absence of actinic light for about 3 hours to about 12 hours.

7 Claims, No Drawings

(56) References Cited

OTHER PUBLICATIONS

Kim, S. et al, "A study of Rose Bengal Against a 2-keto-3-deoxy-d-manno-octulosonate cytidylyltransferase as an Antibiotic Candidate," Journal of Enzyme Inhibition and Medical Chemistry, vol. 35, No. 1, pp. 1414-1421, Dec. 2020. doi: 10.1080/14756366.2020.1751150.
Vilcheze, C. et al, "Resistance to Isoniazid and Ethionamide in *Mycobacterium tuberculosis*: Genes, Mutations, and Causalities," Microbiology Spectrum, Aug. 2014;2(4):MGM2-0014-2013. doi: 10.1128/microbiolspec.MGM2-0014-2013.
Morlock, G.P. et al, "ethA, inhA, and katG loci of Ethionamide-Resistant Clinical *Mycobacterium tuberculosis* Isolates," Antimicrobial Agents Chemotherapy, vol. 47, No. 12, pp. 3799-3805, Dec. 2003. doi: 10.1128/AAC.47.12.3799-3805.2003.
Laborde, J. et al, "Ethionamide Biomimetic Activation and an Unprecedented Mechanism for its Conversion into Active and Non-active Metabolites," Organic & Biometric Chemistry, vol. 14, issue 37, pp. 8848-8858, Oct. 2016. (Abstract only) https://doi.org/10.1039/c6ob01561a.
Lei, T. et al, "Complete Genome Sequence of Hospital-Acquired Methicillin-Resistant *Staphylococcus aureus* Strain WCUH29," Microbiology Resource Announcements, vol. 8, No. 23, pp. e00551-19, Jun. 6, 2019. doi: 10.1128/MRA.00551-19.
Boldrin, F. et al, "Assessing the Role of Rv1222 (RseA) as an Anti-Sigma Factor of the *Mycobacterium tuberculosis* extracytoplasmic Sigma Factor SigE," Scientific Reports, vol. 9:4513, Mar. 14, 2019. doi: https://doi.org/10.1038/s41598-019-41183-4 (Correction published Nov. 22, 2019).
Wu, Q.L. et al, "A Mycobacterial Extracytoplasmic Function Sigma Factor Involved in Survival Following Stress," Journal of Bacteriology, vol. 179, No. 9, pp. 2922-2929, May 1997. doi: https://doi.org/10.1128/jb.179.9.2922-2929.1997.
Tong, H. et al, "A *Streptococcus aquaporin* Acts as Peroxiporin for Efflux of Cellular Hydrogen Peroxide and Alleviation of Oxidative Stress," J Biol Chem., vol. 294, No. 12, pp. 4583-4595, Mar. 22, 2019. doi: 10.1074/jbc.RA118.006877.
Whitcher, J.P. et al, "A Simplified Quantitative Method for Assessing Keratoconjunctivitis Sicca from the Sjögren's Syndrome International Registry," Am J Ophthalmol. vol. 149, No. 3, pp. 405-415, Mar. 2010. doi: 10.1016/j.ajo.2009.09.013.
Siricilla, S. et al, "A New Combination of a Pleuromutilin Derivative and Doxycycline for Treatment of Multidrug-Resistant Acinetobacter baumannii," J. Med. Chem., vol. 60, No. 7, pp. 2869-2878, Apr. 13, 2017. doi.org/10.1021/acs.jmedchem.6b01805.
Siricilla, S. et al, "Discovery of a Capuramycin Analog that Kills Nonreplicating *Mycobacterium tuberculosis* and its Synergistic Effects with Translocase I Inhibitors," The Journal of Antibiotics vol. 68, pp. 271-278, 2015. doi: org/10.1038/ja.2014.133.
Mitachi, K. et al, "Novel FR-900493 Analogues That Inhibit the Outgrowth of Clostridium difficile Spores," ACS Omega, No. 3, pp. 1726-1739, 2018. doi.org/10.1021/acsomega.7b01740.
Mitachi, K. et al, "A Practical Synthesis of a Novel DPAGT1 Inhibitor, aminouridyl phenoxypiperidinbenzyl butanamide (APPB) for in Vivo Studies," MethodsX, No. 6, pp. 2305-2321, 2019. doi.org/10.1016/j.mex.2019.09.031.
"Determining Laboratory Reference Intervals: CLSI Guideline Makes the Task Manageable," Lab Guidelines and Standards, Laboratory Medicine, vol. 40, No. 2, pp. 75-76, Feb. 2009. doi.org/10.1309/LMEHV3HP39QOFJPA.
Mitachi, K. et al, "DPAGT1 Inhibitors of Capuramycin Analogues and Their Antimigratory Activities of Solid Tumors," J. Med. Chem. vol. 63, No. 19, pp. 10855-10878, Oct. 8, 2020. https://doi.org/10.1021/acs.jmedchem.0c00545.
Kaser, M. et al, "Optimized DNA Preparation from Mycobacteria," Cold Spring Harbor Protocols, 2010(4):pdb.prot5408. (Abstract only) doi:10.1101/pdb.prot5408.
Lei, T. et al, "Identification of Target Genes Mediated by Two-Component Regulators of *Staphylococcus aureus* Using RNA-seq Technology," Methods in Molecular Biology, vol. 2069, pp. 125-138, Jan. 1, 2020. (Abstract only) doi:10.1007/978-1-4939-9849-4_10.
Austin, A. et al, "Update on the Management of Infectious Keratitis," Ophthalmology, vol. 124, No. 11, pp. 1678-1689, Nov. 2017. doi: 10.1016/j.ophtha.2017.05.012.
Bassetti, M. et al, "New Antibiotics for Bad Bugs: Where are we?" Annals of Clinical Microbiology and Antimicrobials, 12, No. 22, pp. 1-15, 2013. doi: 10.1186/1476-0711-12-22.
Butler, M.S. et al, "Antibiotics in the Clinical Pipeline in 2013," The Journal of Antibiotics, vol. 66, pp. 571-591, 2013. https://doi.org/10.1038/ja.2013.86.
Woodford, N. et al, "Infections Caused by Gram-Positive Bacteria: A Review of the Global Challenge," Journal of Infection, 59(S1) pp. S4 S16, 2009. DOI: 10.1016/S0163-4453(09)60003-7.
Dupont, H. et al, "Enterococci Increase the Morbidity and Mortality Associated with Severe Intra-Abdominal Infections in Elderly Patients Hospitalized in the Intensive Care Unit," Journal of Antimicrobial Chemotherapy, vol. 66, Issue 10, pp. 2379-2385, Oct. 2011. https://doi.org/10.1093/jac/dkr308.
Alhassan, M.B. et al, "Interventions for Mooren's Ulcer," Cochrane Database Syst Rev. Jan. 22, 2014;(1):CD006131. doi: 10.1002/14651858.CD006131.pub3.
Sharma, A. et al, Review: Emerging Strategies for Antimicrobial Drug Delivery to the Ocular Surface: Implications for Infectious Keratitis, The Ocular Surface, vol. 15, No. 4, pp. 670-679, Oct. 2017. (Abstract only) doi.org/10.1016/j. jtos.2017.06.001.
Teweldemedhin, M. et al, "Bacterial Profile of Ocular Infections: A Systematic Review," BMC Ophthalmology, Nov. 25, 2017;17(1):212. doi: 10.1186/s12886-017-0612-2.
Zheng, X. et al, "Effect of Different Drugs and Drug Combinations on Killing Stationary Phase and Biofilms Recovered Cells of Bartonella henselae in Vitro," BMC Microbiol 20, 87, 2020. https://doi.org/10.1186/ s12866-020-01777-9.
Ginimuge, P.R. et al, "Methylene Blue: Revisited," J Anaesthesiol Clin Pharmacol, vol. 26, No. 4, pp. 517-520, Oct.-Dec. 2010.
Ammerman, N.C. et al, "Clofazimine has Delayed Antimicrobial Activity against *Mycobacterium tuberculosis* both in vitro and in vivo," Journal of Antimicrobial Chemotherapy, vol. 72, No. 2, pp. 455-461, Feb. 2017. https://doi.org/10.1093/jac/dkw417.
Mizutani, T., "Toxicity of Xanthene Food Dyes by Inhibition of Human Drug-Metabolizing Enzymes in a Noncompetitive Manner," Journal of Environmental and Public Health, vol. 2009, Article ID 953952, (9 pages), 2009. doi:10.1155/2009/953952.
Feenstra, R.P. et al, "Comparison of Fluorescein and Rose Bengal Staining," Ophthalmology, vol. 99, No. 4, pp. 605-617, Apr. 1992. https://doi.org/10.1016/S0161-6420(92)31947-5.
Wachter, E. et al, "Topical Rose Bengal: Pre-Clinical Evaluation of Pharmacokinetics and Safety," Lasers in Surgery and Medicine, vol. 32, No. 2, pp. 101-110, 2003. doi:10.1002/1sm.10138.
Gilger, B.C., "A Topical Aqueous Calcineurin Inhibitor for the Treatment of Naturally Occurring Keratoconjunctivitis sicca in Dogs," Veterinary Ophthalmology, vol. 16, No. 3, pp. 192-197, May 2013. https://doi.org/10.1111/ j.1463-5224.2012.01056.x.
Paczkowski, J. et al, "Photophysical Properties of Rose Bengal and its Derivatives (XII)," J Free Radic Biol Med. 1985;1(5-6):341-51. (Abstract only) doi: 10.1016/0748-5514(85)90146-1.
Maker, A.V. et al,"The Potential of Intralesional Rose Bengal to Stimulate T-Cell Mediated Anti-Tumor Responses," J Clin Cell Immunol. Aug. 2015; 6(4):343. doi:10.4172/2155-9899.1000343.
Liu, H. et al, "Intralesional Rose Bengal in Melanoma Elicits Tumor Immunity via Activation of Dendritic Cells by the Release of High Mobility Group Box 1," Oncotarget, vol. 7, No. 25, pp. 37893-37905; May 9, 2016. doi:10.18632/oncotarget.9247.
Patel, S.P. et al, "Percutaneous Hepatic Injection of Rose Bengal Disodium (PV-10) in Metastatic Uveal Melanoma," Journal of Clinical Oncology, 38:15_suppl, 3143-3143, May 2020. DOI: 10.1200/JCO.2020.38.15_suppl.3143.
Kim, Y.S. et al, "Cancer Treatment using an Optically Inert Rose Bengal Derivative Combined with Pulsed Focused Ultrasound," J Control Release. Dec. 20, 2011; 156(3): 315-322. doi: 10.1016/j.jconrel.2011.08.016.

(56) References Cited

OTHER PUBLICATIONS

Qin, Z et al, "Colon Cancer Cell Treatment with Rose Bengal Generates a Protective Immune Response via Immunogenic Cell Death," Cell Death and Disease, vol. 8, No. 7, Feb. 2, 2017, e2584. doi.org/10.1038/ cddis.2016.473.

Perez-Laguna, V. et al, "Antimicrobial Photodynamic Activity of Rose Bengal, Alone or in Combination with Gentamicin, against planktonic and biofilm *Staphylococcus aureus,*" Photodiagnosis and Photodynamic Therapy, vol. 21, Mar. 2018, pp. 211-216. https://doi.org/10.1016/j.pdpdt.2017.11.012.

Uekubo, A. et al, "Effect of Antimicrobial Photodynamic Therapy Using rose bengal and blue light-emitting diode on Porphyromonas gingivalis in vitro: Influence of oxygen during treatment," Laser Therapy, vol. 25, No. 4, Dec. 30, 2016, pp. 299-308. doi: 10.5978/islsm.16-OR-25.

Anju, V.T. et al, "Antimicrobial Photodynamic Activity of Rose Bengal Conjugated Multi Walled Carbon Nanotubes against Planktonic cells and Biofilm of *Escherichia coli,*" Photodiagnosis and Photodynamic Therapy, vol. 24, pp. 300-310, Dec. 2018. doi: 10.1016/j.pdpdt.2018.10.013.

Gavara, R. et al, "Broad-Spectrum Photo-Antimicrobial Polymers Based on Cationic Polystyrene and Rose Bengal," Frontiers in Medicine, vol. 8, article 641646, May 2021. https://doi.org/10.3389/fmed.2021.641646.

Nakonieczna, J. et al, "Rose Bengal-Mediated Photoinactivation of Multidrug Resistant Pseudomonas aeruginosa Is Enhanced in the Presence of Antimicrobial Peptides," Frontiers in Microbiology, vol. 9, article 1949, Aug. 2018. https://doi.org/10.3389/fmicb.2018.01949.

Hirose, M. et al, "Efficacy of Antimicrobial Photodynamic Therapy with Rose Bengal and Blue Light against Cariogenic Bacteria," Archives of Oral Biology, p. 105024, Feb. 2021. doi: 10.1016/j.archoralbio.2020.105024.

Dai, T. et al, "Photodynamic Therapy for Localized Infections—State of the Art," Photodiagnosis Photodyn Ther. 2009; 6(3-4): 170-188. doi:10.1016/j.pdpdt.2009.10.008.

Ghorbani, J. et al, "Photosensitizers in Antibacterial Photodynamic Therapy: An Overview," Laser Therapy, vol. 27, No. 4, pp. 293-302, 2018. https://doi.org/10.5978/islsm.27_18-RA-01.

Kim, Y.S. et al,"Antibacterial Compounds from Rose Bengal-sensitized Photooxidation of beta-caryophyllene," Journal of Food Science, vol. 73, No. 7, pp. C540-C545, Sep. 2008. https://doi.org/10.1111/j.1750-3841.2008.00879.x.

Manoi, D. et al, "Rose Bengal Uptake by E. faecalis and F. nucleatum and Light-Mediated Antibacterial Activity Measured by flow Cytometry," Journal of Photochemistry & Photobiology, B: Biology, vol. 162, pp. 258-265, 2016. DOI: 10.1016/j.jphotobiol.2016.06.042.

Sabbahi, S. et al, "*Staphylococcus aureus* Photodynamic Inactivation Mechanisms by Rose Bengal: Use of Antioxidants and Spectroscopic Study," Applied Water Science, 8(2):56, Apr. 2018.https://doi.org/10.1007/ s13201-018-0693-y.

Santos, A.R. et al, "The Remarkable Effect of Potassium lodide in Eosin and Rose Bengal Photodynamic Action against *Salmonella typhimurium* and *Staphylococcus aureus,*" Antibiotics 2019, 8(4), 211; https://doi.org/10.3390/antibiotics8040211.

Naranjo, A. et al, "Rose Bengal Photodynamic Antimicrobial Therapy for Patients With Progressive Infectious Keratitis: A Pilot Clinical Study," Am J Ophthalmol. Dec. 2019;208:387-396. doi: 10.1016/j.ajo.2019.08.027. Epub Sep. 5, 2019.

Amescua, G. et al, "Rose Bengal Photodynamic Antimicrobial Therapy: A Novel Treatment for Resistant Fusarium Keratitis," Cornea. Sep. 2017;36(9):1141-1144. doi: 10.1097/ICO.0000000000001265.

Martinez, J.D. et al, "Human Corneal Changes after Rose Bengal Photodynamic Antimicrobial Therapy for the Treatment of Fungal Keratitis," Cornea. Oct. 2018; 37(10): e46-e48. doi: 10.1097/ICO.0000000000001701.

Halili, F. et al, "Rose Bengal- and Riboflavin-Mediated Photodynamic Therapy to Inhibit Methicillin-Resistant *Staphylococcus aureus* Keratitis Isolates," Am J Ophthalmol . Jun. 2016;166:194-202. (Abstract only) doi: 10.1016/j.ajo.2016.03.014.

Arboleda, A. et al, "Assessment of Rose Bengal Versus Riboflavin Photodynamic Therapy for Inhibition of Fungal Keratitis Isolates," Am J Ophthalmol. Jul. 2014;158(1):64-70.e2. doi: 10.1016/j.ajo.2014.04.007.

Yorek, M.S. et al, "Corneal Sensitivity to Hyperosmolar Eye Drops: A Novel Behavioral Assay to Assess Diabetic Peripheral Neuropathy," Invest Ophthalmol Vis Sci. May 1, 2016;57(6):2412-9. doi: 10.1167/iovs.16-19435.

Berge, S.M. et al, "Pharmaceutical Salts," Journal of Pharmaceutical Sciences, vol. 66, No. 1, pp. 1-19, Jan. 1977.

Batistela, V.R. et al, "pKa Determinations of Xanthene Derivates in Aqueous Solutions by Multivariate Analysis Applied to UV-Vis Spectrophotometric Data," Spectrochimica Acta Part A: Molecular and Biomolecular Spectroscopy, vol. 79, issue 5, pp. 889-897, Sep. 2011. dx.doi.org/10.1016/j.saa.2011.03.027.

Abelson, M.B. et al, "Normal Human Tear pH by Direct Measurement," Arch Ophthalmol. Feb. 1981;99(2):301. (Abstract only) doi: 10.1001/archopht.1981.03930010303017.

Innamarato, P. et al, "Intralesional Injection of Rose Bengal Augments the Efficacy of Gemcitabine Chemotherapy against Pancreatic Tumors," BMC Cancer, vol. 21, 756, 2021. https://doi.org/10.1186/s12885-021-08522-z.

Thompson, J.F. et al, "Treatment of In-transit Melanoma Metastases using Intralesional PV-10," Melanoma Res. Jun. 1, 2021;31(3):232-241. doi: 10.1097/CMR.0000000000000729.

Swift, L. et al, "Potent in vitro and Xenograft Antitumor Activity of a Novel Agent, PV-10, Against Relapsed and Refractory Neuroblastoma," OncoTargents and Therapy, vol. 12, 2019, pp. 1293-1307. doi:10.2147/ott.s191478.

Kurosu, M. et al, "Antibacterial Activity of Pharmaceutical-Grade Rose Bengal: An Application of a Synthetic Dye in Antibacterial Therapies," Molecules 2022, 27, 322. https://doi.org/10.3390/molecules27010322.

Zuo, H. et al, "Genetic and Phenotypic Diversity of methicillin-resistant *Staphylococcus aureus* Among Japanese Inpatients in the Early 1980s," Scientific Reports, vol. 11, p. 5447, 2021. https://doi.org/10.1038/s41598-021-84481-6.

Lelovic, N. et al, "Application of *Mycobacterium smegmatis* as a Surrogate to Evaluate Drug Leads Against *Mycobacterium tuberculosis,*" J Antibiot (Tokyo), vol. 73, No. 11, pp. 78-789, Nov. 2020. doi: 10.1038/s41429-020-0320-7.

International Search Report re application No. PCT/US22/54076, dated Apr. 25, 2023.

Office Action re Japanese Application No. JP 2024-538697, dated Sep. 2, 2025.

Halili, F. et al, "Rose Bengal- and Riboflavin-Mediated Photodynamic Therapy to Inhibit Methicillin-Resistant *Staphylococcus aureus* Keratitis Isolates," Am J Ophthalmol . Jun. 2016;166:194-202. doi: 10.1016/j.ajo.2016.03.014.

Eye Bank Journal, Japan Eye Bank Association, vol. 22, No. 2, 2018.

Nagai, N., "Formulation Design and Drug Behavior in Eye Drops," Journal of the Japanese Society for Cataract Research, vol. 33, No. 1, pp. 32-36, 2021. https://doi.org/10.14938/cataract.13-004.

Ferreira, T.A.C. et al, "Antimicrobial Activity of Topical Dyes used in Clinical Veterinary Ophthalmology," Veterinary Ophthalmology, vol. 23, No. 3, pp. 497-505, 2020. doi: 10.1111/vop.12746.

Supplementary European Search Report re Application No. EP 22917281.2, dated Oct. 24, 2025.

Lanier, O.L. et al, "Review of Approaches for Increasing Ophthalmic Bioavailability for Eye Drop Formulations," AAPS PharmSciTech 22, 107, 2021. https://doi.org/10.1208/s12249-021-01977-0.

* cited by examiner

HALOGENATED XANTHENE-CONTAINING TOPICAL ANTI-GRAM-POSITIVE BACTERIAL OPHTHALMIC COMPOSITION AND METHOD

CROSS-REFERENCE TO RELATED APPLICATION

This application claims priority to U.S. application Ser. No. 63/294,252, filed on Dec. 28, 2021, whose disclosures are incorporated herein by reference.

BACKGROUND ART

Corneal disease is a leading cause of monocular blindness worldwide, especially affecting marginalized populations. Corneal opacities, which are largely caused by infectious keratitis, are the fourth leading cause of blindness globally and are responsible for 10% of avoidable visual impairment in the world's least resourced countries. About two million people develop a corneal ulcer every year in India alone. In the United States, infectious keratitis is often associated with contact lens wear, but in under-resourced countries it is more commonly caused by ocular trauma sustained during agricultural work. [Austin et al., *Ophthalmology* 124(11):1678-1689 (2017).]

A corneal ulcer, keratitis, is an open sore on the cornea and is a common human eye condition. It can be caused by trauma, particularly with vegetable matter, as well as chemical injury, contact lenses and infections. Other eye conditions can cause corneal ulcers, such as entropion, distichiasis, corneal dystrophy, and keratoconjunctivitis sicca (dry eye).

Many micro-organisms cause infective corneal ulcer. Among them are bacteria, fungi, viruses, protozoa, and *Chlamydia*.

Bacterial keratitis can be caused by a number of bacteria, including *Staphylococcus aureus, Streptococcus viridans, Escherichia coli*, Enterococci, *Pseudomonas, Nocardia, N. gonorrhoea* and many other bacteria. The increasing emergence of multidrug-resistant (MDR) Gram-positive bacteria is a major public health threat [Bassetti et al., *Annal. Clinic. Microbiol. Antimicrob.* 12:1-15 (2013); Butler et al., *J. Antibiot.* 66:571-591 (2013); and Woodford et al., *J. Infect.* 59:S4-16 (2009)]. Particularly, MDR strains of *Staphylococcus, Enterococcus*, and *Streptococcus* spp. have a significant impact on morbidity and mortality [Dupont et al., *J. Antimicrob. Chemother.* 66:2379-2385 (2011)].

Fungal keratitis causes deep and severe corneal ulceration. It is typically caused by *Aspergillus* sp., *Fusarium* sp., *Candida* sp., as also *Rhizopus, Mucor*, and other fungi. The typical feature of fungal keratitis is slow onset and gradual progression, where signs are much more than the symptoms. Small satellite lesions around the ulcer are a common feature of fungal keratitis and a condition involving inflammatory cells in the anterior chamber of the eye (hypopyon) is observed.

Viral keratitis causes corneal ulceration. It is caused most commonly by herpes simplex, herpes zoster, and adenoviruses. It can also be caused by coronaviruses and many other viruses.

Herpes virus causes a dendritic ulcer, which can recur and relapse over the lifetime of an individual. Herpes simplex virus (HSV) keratitis affects an estimated 500,000 people in the United States and an estimated 1.5 million globally. It is the most common cause of unilateral infectious corneal blindness in much of the developed world. [Austin et al., *Ophthalmology* 124(11):1678-1689 (2017).]

Viral keratitis differs from bacterial and fungal keratitis in that it can become chronic and recurrent. Besides being a painful, sight-threatening infection, HSV keratitis has been shown to significantly impact quality of life even when patients are not experiencing an active infection. Less common forms of viral keratitis include varicella-zoster virus (VZV) keratitis, and cytomegalovirus (CMV) keratitis. [Austin et al., *Ophthalmology* 124(11):1678-1689 (2017).]

Protozoa infection such as *Acanthamoeba* keratitis is characterized by severe pain and is associated with contact lens users swimming in pools.

Superficial ulcers involve a loss of part of the epithelium. Deep ulcers extend into or through the stroma and can result in severe scarring and corneal perforation. Descemetoceles occur when the ulcer extends through the stroma. This type of ulcer is especially dangerous and can rapidly result in corneal perforation, if not treated in time.

The location of the ulcer depends somewhat on the cause. Central ulcers are typically caused by trauma, dry eye, or exposure from facial nerve paralysis or exophthalmos. Entropion, severe dry eye, and trichiasis (inturning of eyelashes) may cause ulceration of the peripheral cornea. Immune-mediated eye disease can cause ulcers at the border of the cornea and sclera. These include Rheumatoid arthritis, rosacea, and systemic sclerosis, which lead to a special type of corneal ulcer called Mooren's ulcer. Mooren's ulcer has a circumferential crater like depression of the cornea, just inside the limbus, usually with an overhanging edge.

Proper diagnosis is essential for optimal treatment. The cause of the ulcer is to be decided; whether infective or non-infective.

Bacterial corneal ulcer normally requires intensive fortified antibiotic therapy to treat the infection. Fungal corneal ulcers require intensive application of topical anti-fungal agents. Viral corneal ulceration caused by herpes virus may respond to anti-viral agents like topical acyclovir ointment instilled at least five times a day. Alongside, supportive therapy like pain medications are typically administered, including topical cycloplegics like atropine or homatropine to dilate the pupil and thereby stop spasms of the ciliary muscle.

Superficial ulcers may heal in less than a week. Deep ulcers and descemetoceles may require conjunctival grafts or conjunctival flaps, soft contact lenses, or corneal transplant. Proper nutrition, including protein intake and vitamin C are usually advised. In cases of keratomalacia, where the corneal ulceration is due to a deficiency of vitamin A, supplementation of the vitamin A by oral or intramuscular route is given. Drugs that are usually contraindicated in corneal ulcer are topical corticosteroids [Alhassan et al., *Cochrane Database Syst Rev.* 1 (1):CD006131 (2014)] and anesthetics—these should not be used on any type of corneal ulcer because they prevent healing, may lead to superinfection with fungi and other bacteria, and will often make the condition much worse.

'Red eye', 'conjunctivitis' and 'corneal ulcer/keratitis' were among the problems commonly referred to. Conjunctivitis is a common condition that causes dilation of the conjunctival blood vessels and results in inflammation. Both viral and bacterial conjunctivitis present with a red eye and are highly contagious. Assessment should include checking visual acuity and examination with a torch or slit lamp. Fluorescein drops should be instilled in the conjunctival sac and the eye viewed with the cobalt blue light of the slit lamp or funduscope, to rule out any signs of corneal ulceration or infection.

Viral conjunctivitis is the most common cause of infectious conjunctivitis. This infection is more common in adults than in children. Most cases are caused by adenovirus. Occasionally, herpes simplex or zoster virus is responsible. Patients can generally be advised that viral conjunctivitis is self-limiting, as there are no specific treatments.

Bacterial conjunctivitis, although a less frequent cause of conjunctivitis, is more common in children. The most common bacteria are *Haemophilus influenza, Streptococcus pneumoniae*, and *Staphylococcus aureus*. The use of antibiotic eye drops is associated with improved rates of clinical and microbiological remission. A broad-spectrum topical antibiotic is often recommended.

Infection of the cornea (microbial keratitis) is an ophthalmic emergency requiring immediate attention as it can progress rapidly. It is one of the most common causes of visual impairment in working age adults. In the USA, about 30,000 cases of microbial keratitis are reported annually [Sharma et al., *Ocul Surf* 15:670-0679 (2017)].

Bacterial infection is the most common cause of infectious keratitis. Common causal bacteria include *S. aureus*, coagulase-negative staphylococci, *S. pneumoniae* and *Pseudomonas aeruginosa* [Teweldmedhin et al., *BMC Ophthalmol* 17:212 (2017)]. *P. aeruginosa* is the most common microorganism implicated in bacterial keratitis among contact lens wearers.

Although bacterial ulcers are usually responsive to treatment with available topical antibiotic drops as discussed below, an increase in the rates of antibiotic resistant infections such as methicillin resistant *Staphylococcus aureus* (MRSA) in North America has caused concern. The United States Center for Disease Control (CDC) estimates that 2 million people are infected with drug resistant microbes each year. Approximately 80% of ocular isolates of MRSA in the US have been reported to be resistant to the most commonly prescribed antibiotic class, the fluoroquinolones. [Austin et al., *Ophthalmology* 124(11):1678-1689 (2017).]

Topical antibiotics are the current mainstay of treatment and options include monotherapy with fluoroquinolones (ciprofloxacin 0.3% or ofloxacin 0.3% 1-2 drops hourly for 48 hours, then every 4 hours until healed) or fortified aminoglycoside/cephalosporin combinations (fortified cefalotin 5% plus gentamicin 0.9% 1-2 drops hourly for 48 hours, then reduce frequency according to treatment response). These regimens have similar effectiveness, but fluoroquinolones reduce the risk of chemical conjunctivitis and ocular discomfort. Compared to ofloxacin, ciprofloxacin increases the risk of white corneal precipitates. Occasionally, corneal grafting may be needed to eradicate the organism or repair damage. Although apparently effective, hourly treatment with eye drops is a difficult regimen to follow for many patients.

Chloramphenicol is the most common first-line antibiotic prescribed for red eye. Several commercial products are available, both as eye drops and as an ophthalmic ointment. Illustratively, an ophthalmic solution containing chloramphenicol at 0.25% and 0.5% and an ophthalmic ointment containing chloramphenicol at 1% are available under the trade name $^{Pr}$PENTAMYCETIN® from Sandoz Canada Inc.

The dosage and administration instructions for the ophthalmic solution state only "2 drops of the ophthalmic solution to the affected eye(s) every 3 hours or more often if necessary". The dosage and administration instructions for the ophthalmic ointment state: "A small amount of ointment to the affected eye(s) every 3 hours or more often if necessary." Again, frequently-repeated administration is required. [*Prescribing Information, $^{Pr}$PENTAMYCETIN®, $^{Pr}$PENTAMYCETIN/HC®* Sandoz Canada Inc., Date of Revision: Jun. 14, 2918.]

Naturally occurring and synthetic dyes have been applied as antibacterial or antiprotozoal agents [Zheng et al., *BMC Microbiol* 20 (2020]. For example, methylene blue and clofazimine are still considered to be important orphan drugs [Ginimuge et al., *J. Anaesthesiol. Clin. Pharmacol.* 26:517-520 (2010); and Ammerman et al., *J. Antimicrob. Chemother.* 72:455-461 (2017)].

Rose bengal (RB) is a bright rose-red xanthene derivative compound that was first synthesized in the 19$^{th}$ century as a wool dye and subsequently used as a food dye in Japan (food red no. 105) [Mizutani et al., *J. Environ. Public Health.* 2009, 953952]. More particularly, RB is a derivative of the xanthene compound fluorescein. Compared to fluorescein, RB has two types of additional halogens: four chloride and four iodide substituents.

The use of RB for the visual diagnosis of human ocular surface damage (via ocular instillation) was first described in 1914 [Feenstra et al., *Ophthalmology* 99:606-617 (1992)]. RB was later introduced as an intravenously-administered, relatively rapid, diagnostic aid to evaluate the functional capacity of a human liver after a single 100 mg dose [Wachter et ala., *Lasers Surg Med.* 32:101-110 (2003)]. In 1971, $^{131}$I RB (Robengatope®, rose bengal sodium $^{131}$I injection USP) was approved by the U.S. Food and Drug Administration (FDA) for use as a diagnostic aid in determining liver function [Baroyan et al., *Eksperimental'naya Meditsina* (Riga) 20:74-78 (1985); and Mincev et al., *Folia Medica* (Plovdiv) 16:35-41 (1974)].

In 2009, Robengatope's manufacturer Bracco Diagnostics Inc. formally withdrew the RB diagnostic product from the U.S. market because of the emergence of newer methods of liver imaging, such as computed tomography. In 1974, Barnes-Hind Pharmaceuticals Inc. (Barnes-Hind) introduced a medical device product of 1% RB in an aqueous solution for the disclosure of corneal injury, the diagnosis of keratitis, keratoconjunctivitis, and sicca, and the detection of foreign bodies in the eye [Gilger et al., *Vet. Ophthalmol.* 16:192-197 (2013)]. In 1981, Barnes-Hind introduced ophthalmic strips of the same concentration for the same indications. Although both diagnostic products were accepted by the U.S. Food and Drug Administration (FDA) for marketing, neither the solution and strip devices nor their respective claims were approved because their introductions predated formal FDA review and approval.

Commercial-grade RB, with marketed dye contents that can vary between 80% and 95% RB, including gross contaminants and substance-related impurities, is manufactured using an historical process developed by Gnehm in the 1880s. It is thought that RB used in diagnostic applications is a commercial-grade RB that contains some impurities [Paczkowski et al., *Free Radic. Biol. Med.* 1:341-351 (1985)]. The United States Pharmacopeia (USP) previously listed RB as an analytical standard. RB was removed from the USP in 2019. Thus, commercial-grade RB lacks relevance in the context from modern diagnostic and therapeutic settings. Therefore, it poses significant regulatory challenges to validate RB for application to the treatment of human diseases.

U.S. Pat. Nos. 8,530,675, 9,273,022 and 9,422,260 to Singer et al. describe and claim the synthesis of highly purified rose bengal, as well as similarly purified similar compounds containing different halogen substituents and different numbers of those halogen substituents, as well as their lactone forms. Those compounds are collectively referred to herein as "halogenated xanthenes".

Rose bengal (RB) dye (4,5,6,7-tetrachloro-2',4',5',7'-tetraiodofluorescein) has been clinically investigated for the treatment of melanoma and the other solid cancers [Maker et al., *J. Clin. Cell. Immunol.* 6:343-349 (2015; Liu et al., *Oncotarget.* 7:37893-37905 (2016); Patel et al., *J. Clin. Oncol.* 38:3143 (2020); Kim et al., *J. Control. Release.* 156:315-322 (2011); and Qin et al., *Cell Death Dis.* 8:e2584 (2017)]. Photodynamic antibacterial properties of RB have been sporadically reported [Pérez-Laguna et al., *Photodiagnosis Photodyn. Ther.* 21:211-216 (2018); Uekubo et al., *Laser Ther.* 25:299-308 (2016); Anju et al., *Photodiagnosis Photodyn. Ther.* 24:300-310 (2018); Gavara et al., *Front. Med.* 8:494 (2021); Joanna et al., *Front. Microbiol.* 9:1949 (2018); Hirose et al., *Arch. Oral Biol.* 122:105024 (2021); Dai et al., *Photodiag. Photodyn. Ther.* 6:170-188 (2009); Ghorbani et al., *Laser Ther.* 27:293-302 (2018); Kim et al., *J. Food Sci.* 73:C540-545 (2008); Manoi et al., *J. Photochem. Photobiol. B.* 162:258-265 (2016); Nakonieczna et al., *Front. Microbiol.* 9:1949 (2018); Sabbhi et al., *Appl. Water Sci.* 8:56 (2018); Santos et al., *Antibiotics* 8:211 (2019); and Worzella et al., In *Cancer Cell Culture*; Humana Press: Totowa, NJ, USA, 285-291. (2011)].

For example, Dees et al. U.S. Pat. No. 8,974,363 teaches use of a topical formulation of RB at 10-100 μM (i.e., 10 μg/mL to 100 μg/mL) in conjunction with green light irradiation in the 500-600 nm wavelength band against Gram-positive and Gram-negative antibiotic-resistant bacteria without specifics as to the light source, its intensity or duration of irradiation.

Naranjo et al., *Am J Ophthalmol* 208:387-396 (2019), reported the use of rose bengal photodynamic antimicrobial therapy (RB-PDAT) on the eyes of 18 patients with progressive infectious keratitis that were unresponsive to standard therapy. Compositions containing 0.1 or 0.2% rose bengal (RB) were applied to de-epithelized corneas for 30 minutes followed by irradiation with 5.4 J/cm$^2$ of green light from a LED source for 15 minutes. *Acanthamoeba* (an amoeba) was the most frequently found microbe (10/17; 59%), followed by *Fusarium* spp. (a fungus; 4/17; 24%), *Pseudomonas aeruginosa* (a Gram-negative bacterium; 2/17; 12%) and Curvularia spp. (a fungus; 1/17; 6%) and one patient had no confirmed microbiologic diagnosis. Successful RB-PDAT (avoidance of therapeutic keratoplasty) was reported achieved in 72% of the cases, with an average time to clinical resolution (decreased pain and inflammation with reepithelization and infiltrate resolution) of 46.9±26.4 days after RB-PDAT.

Amescua et al., *Cornea* 36(9):1141-1144 (2017), teach that rose bengal (RB) at about 0.1% that was photoactivated using 15 minutes of irradiation at 375 nm or 518 nm could inhibit the fungal growth of multidrug-resistant *Fusarium keratoplasticum* in vitro. Following multiple successive anti-fungal medication treatments, a study was conducted using an above concentration of RB dripped onto a *Fusarium keratoplasticum*-infected, debrided cornea epithelium of a human patient for 30 minutes followed by irradiation using light at 518 nm to provide a total energy of 0.9 J/cm$^2$. Resolution of pain was noted 36 hours post irradiation, and the corneal infiltrate shrank over the next two weeks. Four days after treatment, the infiltrate was approximately 1 mm smaller in all directions.

At post irradiation treatment day 13, the infiltrate was almost resolved, and a second session of rose bengal RB-irradiation treatment (1.8 J/cm$^2$) was performed. After topical corticosteroid treatment, by day 246 after the first RB treatment, the patient demonstrated a healthy and quiet ocular surface of the treated eye and a clear cornea. A follow-up study of the treated patient's eye is reported in Martinez et al., *Cornea* 37(10):e46-e48 (2018).

Halili et al., *Am J Ophthalmol* 166:194-202 (2016), reported in vitro studies of patient-isolated methicillin-resistant *Staphylococcus aureus* (MRSA) on agar using RB dissolved in high-purity water at 0.1 and 0.03% in the dark, under ambient room light for 30 minutes and under LED green light irradiation for 34 minutes to provide 5.4 J/cm$^2$. Samples were thereafter grown in a light-protected box for 72 hours in an incubator. Complete growth inhibition of both MRSA strains was demonstrated (1) for both rose bengal concentrations under ambient and green LED irradiation, and (2) for the 0.1% rose bengal in the dark. The 0.03% rose bengal in dark conditions showed complete inhibition of strain 2 but incomplete inhibition of strain 1.

Arboleda et al., *Am J Ophthalmol* 158(1):64-70 (2014), reported, inter alia, on the in vitro growth inhibition of fungal keratitis patient isolates using RB in irradiation (518 nm; 5.4 J/cm$^2$) and dark conditions followed by three days of incubation. Isolates of *Fusarium solani, Aspergillus fumigatus* and *Candida albicans* were studied. Data from that study are summarized in the table below.

| | Day 3 Growth Inhibition Percentage | | | |
|---|---|---|---|---|
| Organism | RB + 518 nm Irradiation | RB Only | Only 518 nm Irradiation | Fungus only |
| *F. solani* | 78.2 ± 2.1 | 7.3 ± 1.1 | 6.8 ± 9.3 | 9.8 ± 4.7 |
| *A. fumigattus* | 79.8 ± 9 | 6.6 ± 0. | 0.6 ± 0.2 | 0 |
| *C. albicans* | 95.6 ± 3 | 42.2 ± 3.7 | 35.6 ± 6.7 | 24.2 ± 2.6 |

As disclosed hereinafter, the present invention provides a gentle and more easily-used treatment as is needed. In addition, the treatment contemplates use in the substantial absence of light that produces an identifiable or measureable change when it interacts with matter (actinic light), as when the treated subject is asleep with her/his eyes closed.

BRIEF SUMMARY OF THE INVENTION

In one aspect, the present invention contemplates an ophthalmic system of an actinic light-opaque vessel that contains a topical ophthalmic composition of a halogenated xanthene (fluorescein) such as rose bengal or a pharmaceutically acceptable salt, amide or ester thereof dissolved or dispersed in an aqueous ophthalmic carrier and present in a bacterial keratitis-treating effective concentration of about 0.2 μg/mL to about 50 μg/mL (or about 0.00002 to about 0.005 wt. %) in the composition. In preferred practice, the composition has a pH value of about 6.5 to about 7.6 and preferably about 7.0 to about 7.4, the pH value of normal tears. A contemplated composition preferably further includes thickening agent and an electrolyte. More preferably, hyaluronic acid is also present.

In another aspect of the invention, a mammalian subject in need is treated with an above topical ophthalmic composition by placing a keratitis-treating effective amount of that composition, such as one or two drops per eye, onto the corneal surface of the subject's microbially-infected eye in the substantial absence of actinic light, and the so-treated subject is thereafter maintained in the absence of actinic light for a period of about 3 to about 12 hours. The treatment is typically administered just prior to the mammalian subject retiring to sleep. This treatment regimen is typically repeated a plurality of times until the microbial infection has been overcome.

As used herein, the phrase "actinic light" denotes light that can cause a photochemical reaction of one or more of the ingredients of topical ophthalmic composition. In accordance with this definition, the actinic light is of a wavelength that is absorbed by a recipient molecule of the composition and there is a sufficient flux of photons of the absorbed wavelength to cause a detectable chemical reaction induced in or by the absorbing recipient halogenated fluorescein molecule. Illustrative chemical reactions include decomposition, and photosensitization.

The term "substantial absence of actinic light" is used herein to mean that, after application to the infected eye, the composition is subjected to ambient light for a time period of about two minutes or less. Thus, after application, the eye lid is closed, a light-blocking patch is placed over the treated eye, ambient light is shut off, or the like. Similarly, there is an insufficient flux of photons of an absorbed wavelength to cause a detectable chemical reaction induced in or by the absorbing recipient halogenated fluorescein molecule.

The microbial source of infection can bacterial, viral, fungal or amoebic. Preferably, the source of infection is bacterial, and an infecting bacterium is preferably a Gram-positive bacterium.

DETAILED DESCRIPTION OF PREFERRED EMBODIMENTS

The present invention, in one aspect, contemplates an ophthalmic system of a vessel opaque to actinic light that contains a topical ophthalmic composition of a halogenated xanthene (fluorescein) such as rose bengal or a pharmaceutically acceptable salt, amide or ester thereof dissolved or dispersed in an aqueous ophthalmic carrier and present in a keratitis-treating effective concentration of about 0.2 μg/mL to about 50 μg/mL (or about 0.00002 to about 0.005 wt. %) in the topical ophthalmic composition. Preferably, the concentration of halogenated fluorescein (xanthene) is about 0.5 μg/mL to about 20 μg/mL. In preferred practice, the composition has a pH value of about 6.5 to about 7.6, and more preferably about 7.0 to about 7.4, the pH value of normal tears. A contemplated composition preferably further includes a thickening agent and an electrolyte.

It is noted that a contemplated composition contains about one-tenth to about one thousandth the concentration of halogenated xanthene compared to that of the rose bengal used in the before-discussed Naranjo et al., Amescua et al., Martinez et al., Halili et al., and Arboleda et al. papers.

More preferably, hyaluronic acid, a polymer of disaccharides composed of D-glucuronic acid and N-acetyl-D-glucosamine, linked via alternating β-(1→4) and β-(1→3) glycosidic bonds is also present. Hyaluronic acid provides some thickening, buffering and tonicity to the composition, and helps maintain water of the applied composition in contact with the surface of the eye.

In another aspect of the invention, a mammalian subject in need is treated with an above topical ophthalmic composition by placing a keratitis-treating effective amount of that composition, such as one or two drops per eye, onto the surface of the subject's microbially-infected eye in the absence of additionally-provided actinic light, and the so-treated subject is thereafter maintained in the absence of actinic light for a period of about 3 to about 12 hours. The treatment is typically administered just prior to the mammalian subject retiring to sleep. The use of an actinic light-opaque eye patch to cover the treated eye following administration can also be followed when the treated subject is or is expected to be in the presence of actinic light after administration. This treatment regimen is typically repeated a plurality of times until the microbial infection has been overcome.

Topical Ophthalmic Pharmaceutical Composition

Aqueous Ophthalmic Carrier

A contemplated composition is primarily (by weight) an aqueous ophthalmic carrier in which other ingredients are dissolved or dispersed. The principal component of the composition is sterile water, such as sterile water for injection USP.

A contemplated composition has at least one builder or thickener present at a level sufficient to provide a viscosity of about 10 to about 300 cps, and preferably about 30 to about to 120 cps, and more preferably about 50 to about 80 cps. Typical thickeners are polymers although solvents such as glycerin and propylene glycol can also provide some thickening action to the composition.

Glycerin and propylene glycol alone or together can comprise zero to about 2.5 percent by weight of the composition. More preferably one or both together is present at about 0.4 to about 2 percent by weight. Each of glycerin and propylene glycol is miscible with water.

A contemplated topical ophthalmic composition contains one or more dissolved solutes sufficient to provide the composition with an osmolality (Osm) of the medicament composition of about 270 mOsm/kg to about 340 mOsm/kg osmolality is provided, and preferably about 300 mOsm/kg to 325 mOsm/kg, which is about the range of osmolalities exhibited by human tears.

At least some of that osmolality can be obtained by the presence of water-soluble sodium, potassium, calcium and magnesium chlorides, phosphates, and nitrates. Sodium, such as in the form of sodium chloride, is a preferred embodiment as the electrolyte due to its inherent physiologic compatibility. It is preferable that such an electrolyte be present in the composition at a concentration of about 0.1 to about 2 percent, and more preferably at a concentration of about 0.5 to about 1.5 percent, more preferably at a concentration of about 0.8 about 1.2 percent, and most preferably at a concentration of approximately 0.9 percent. The osmolality of aqueous 0.9 N sodium chloride is 308 mOsmol/liter.

When the subject in need of treatment presents with swelling of the cornea, a hypertonic composition containing about 2 percent to about 5 percent sodium chloride can be utilized to lessen the corneal swelling while treating the infection. The osmolality of eye-treating compositions containing 2 and 5 percents sodium chloride were calculated to be 684 and 1711 mOsm, respectively. [Yorek et al., *Invest Ophthalmol Vis Sci.* 57:2412-2419 (2016)]. Those illustrative products are sold under the trademark Muro 128® by Bausch & Lomb (Bridgewater, New Jersey).

A low molecular weight poly(ethylene glycol) (PEG) such as PEG 400 or PEG 1000 can provide lubrication and some relief from dry eye symptoms to a composition. These polymers also add a relatively small amount of osmolality due to their lack of ionic charge. Depending upon the other solutes present in a contemplated composition, a low molecular weight PEG can be absent or present at about 1 to about 10 mg/mL.

Dextran, a complex branched, non-ionically charged poly-α-d-glucoside of microbial origin having glycosidic bonds that are predominantly C-1→C-6, with branches from α-1,3 linkages. Dextran chains are of varying lengths (from about 3 to about 2000 kilodaltons). Two commonly used dextrans are referred to as dextran 40 and dextran 70 in view of their molecular weights of about 40,000 and 70,000 kDa, respectively.

Dextrin is a water-soluble, straight chain polyglucose tethered by α-1,4 or α-1,6 linkages. Dextrins are mixtures produced by the hydrolysis of starch and glycogen and are free of ionic charge. The characteristic branching distinguishes a dextran from a dextrin, which is a straight chain glucose polymer tethered by α-1,4 or α-1,6 linkages.

Like the PEGs, being uncharged, dextrans and dextrins present in a contemplated composition do not tend to greatly change the composition's osmolality. Dextrans can provide some lubrication to the eye and can be absent of present at about 0.5 to about 2 mg/mL.

Poly(vinylpyrrolidone) that is often sold commercially as povidone is another non-ionically charged polymer that, like the dextrans, has found use as a blood extender for intravenous use, in ophthalmic medicaments, and does not appreciably alter a contemplated composition's osmolality when present. Povidone when present is present at about 1 to about 2 mg/mL, and more preferably at about 7 to about 15 mg/mL.

A still further useful non-ionic polymer is hydroxypropyl methylcellulose (HPMC) also sold commercially as hypromellose. U.S. Pat. No. 5,679,713 teaches the use of a dry eye-treating active agent cholinergic compound along with hypromellose, methyl cellulose, poly(vinyl alcohol), or hyaluronic acid could be used in a pharmaceutical composition. The above patent's results-free example utilized methyl cellulose at 0.5-1 percent by weight and poly(vinyl alcohol) at 1.4 percent by weight.

Another water-soluble non-ionic polymeric thickener is hydroxyethyl cellulose (HEC). This material is available in several molecular weights that provide different amounts of thickening per wt % present. One source of HEC sold under the name Natrosol™ 250 is Ashland Specialty Chemicals of Covington, KY.

The commercially available dry eye medication sold under the tradename Refresh® Tears® and Refresh® Relieva™ both contain anionic carboxymethyl-cellulose sodium at 0.5 percent as an active ingredient, with the Refresh® Relieva™ product also containing glycerin as an active ingredient at 0.9 percent. The active ingredients are present along with a number of inactive ingredients dissolved in purified water. These products are sold by Allergan, Inc. an AbbVie company (North Chicago, IL).

Hyaluronic acid (HA) is an anionic, non-sulfated glycosaminoglycan distributed widely throughout connective, epithelial, and neural tissues. It is polymer of repeating units composed of D-glucuronic acid and N-acetyl-D-glucosamine, linked via alternating β-(1→4) and β-(1→3) glycosidic bonds. It is unique among glycosaminoglycans as it is non-sulfated and can have molecular weight of several million Daltons. Because it is anionic and typically contains several carboxyl groups per molecule, HA can have a relatively large effect on the osmolality of a contemplated composition.

Another anionic thickening polymer is partially neutralized water-dispersible carboxymethyl cellulose. This material is available from many suppliers in differing molecular weights to provide different viscosities per given weight percentage in water.

The phrase "partially neutralized" is used in conjunction with carboxyl group-containing polymers whose carboxyl functionalities are reacted with a base to form anionically charged carboxylate groups and aid in providing the polymer with water-solubility or dispersibility.

Additional anionic thickening agents can also be used such as the partially neutralized cross-linked acrylic acid, methacrylic acid and co-polymers such as the water-soluble cross-linked acrylate polymers of one or more of U.S. Pat. Nos. 3,074,852, 3,330,729 and 4,226,848 and exemplified by the material sold under the trademark CARBOLOL® 934P NF or 974P NF by Lubrizol Corp., Wickliffe, Ohio. These materials are acrylic acid homopolymers cross-linked with a polyalkenyl polyether such as allyl sucrose or allyl pentaerythritol, with each cross-linker containing an average of at least three allyl groups per molecule. Both polymers are reportedly water-soluble and provide viscosities at a pH value of 7.5 when present at 0.5 weight percent. The 934P NF is polymerized in benzene, whereas the 974P NF is polymerized in ethyl acetate as solvents.

Another useful class of thickener is a water-swellable but water-insoluble cross-linked acrylic polymer that is described in U.S. Pat. Nos. 3,202,577 and 4,615,697 and is often referred to in the literature as polycarbophil and as a bioadhesive. These polymers can be defined as a reaction product of the copolymerization of at least 80 weight percent monoethylenically unsaturated carboxy-functional monomer and about 0.05 to about 1.5 weight percent of a cross-linking agent that is 3,4-dihydroxy-1,5-hexadiene, or 2,5-dimethyl-1,5-hexadiene. The carboxyl groups of this polymer are also at least partially neutralized at the p value of the composition.

These bioadhesive polymers are free of polyalkenyl polyether cross-linkers discussed before. The remaining monomers that can be present to constitute 100 percent by weight of the monomers are discussed below.

In addition to the above two ingredients, a bioadhesive polymer can also include polymerized monoethylenically unsaturated repeating units such as $C_1$-$C_6$ alkyl esters of one or more of the above-described acids such as hexyl acrylate, butyl methacrylate and methyl crotonate; hydroxyalkylene-functional esters of the above-described acids that contain a per molecule average of 1 to about 4 oxyalkylene groups containing 2-3 carbon atoms such as hydroxyethyl methacrylate, hydroxypropyl acrylate and tetraethylene glycol monoacrylate; methacrylamide, acrylamide and their $C_1$-$C_6$ mono- and di-alkyl derivatives such as N-methyl acrylamide, N-butyl methacrylamide and N,N-dimethyl acrylamide; styrene; and the like as are known in the art as being copolymerizable with the above described carboxyl functionality-containing monomers and cross-linking agents. The bioadhesive polymers most preferably are prepared from only the monoethylenically unsaturated carboxy-functional monomer and the cross-linking agent.

A bioadhesive useful herein can be prepared by conventional free radical polymerization techniques utilizing initiators such as benzoyl peroxide, azobisisobutyronitrile, and the like, and can also be polymerized in an aqueous medium, and are not agglomerated by steam action. Exemplary preparations of useful bioadhesives are provided in the two patents cited immediately above, whose disclosures are incorporated herein by reference.

As noted previously, the bioadhesives can be polymerized in an aqueous medium. In preferred practice that aqueous medium is a saturated solution of an alkaline earth metal salt such as magnesium sulfate.

The alkaline earth metal salt serves at least two functions. First, it increases the density of polymerization medium so that the polymerized bioadhesive floats on the surface of the aqueous medium and can be easily removed therefrom.

Second, the use of magnesium sulfate, in particular, reduces the swelling of the bioadhesive in the aqueous medium so that polymerization and recovery are facilitated. Bioadhesives typically contain about 0.5 to about 1 percent of the alkaline earth metal ion after several water rinses of the polymer.

U.S. Pat. No. 5,221,722 teaches the preparation of what may be called an enhanced polycarbophil. This polymer is prepared in a solvent selected from acetone and alkyl acetates containing 1 to 6 carbon atoms in the alkyl group in the presence of a suitable initiator and divinyl glycol cross-linker such as 3,4-dihydroxy-1,5-hexadiene. Polycarbophil prepared in this manner is said to have the attributes of bioadhesion, as well as having small particle size without grinding and viscosity of above 20,000 cPs when 1% by weight mucilages thereof are measured in water.

To prevent gelling of the polymer and to promote discrete particle formation during polymerization, at least a part of the carboxyl groups are taught to be neutralized with a group I-A metal compound in the form of a hydroxide, oxide, or carbonate, and the like. Examples of these include sodium, potassium, and the like, as well as reaction with ammonia and certain amines including morpholine; mono, di, and triethanolamine; mono-propanolamine; and other amines where the partial polymeric salt is less soluble in the reaction medium. Preferably, greater than 0.1 percent by weight of the carboxyl groups on the monomer are neutralized or formed into a salt of the above listed materials. More preferably, greater than 1 percent by weight and up to about 10 percent by weight of the carboxyl groups are neutralized or converted to the equivalent salt prior to polymerization, especially less than about 5 percent.

The above-described synthesis is reported to have provided polymer with an average particle size of less than 10μ, such that the particles will pass through a Mesh No. 635 (ASTM-E11). One commercial supplier is The Lubrizol Corporation, above, which sells the polymer for medical uses under the name Noveon® AA-1, Polycarbophil, USP.

The specific amount of any above polymer is not as relevant as is the effect of the polymer as a thickening agent and or bioadhesive. Thus, the amounts of the polymers used typically differ among themselves because they have differing thickening and bioadhesive abilities. Generally speaking, a thickeningly-effective and/or a bioadhesively-effective amount is used.

Halogenated Xanthene (Fluorescein)

A halogenated xanthene (fluorescein) compound of a contemplated topical ophthalmic composition can be a compound of Formula 1, below, in which $R_1$ is independently F, Cl, Br, I, H or $C_1$-$C_4$ alkyl; $R_2$, $R_3$, $R_4$, and $R_5$ are independently Cl, H or I with at least one substituent selected from $R_2$, $R_3$, $R_4$, $R_5$ being I; and $R_6$ is independently H or $C_1$-$C_4$ alkyl; $R^{11}$ is H or $C_1$-$C_4$ alkyl; $R^{12}$ is H or $C_1$-$C_7$ acyl; and all (a) tautomeric forms; (b) atropisomers, (c) closed lactone forms as depicted in Formula 2 (below), (d) enantiomers of lactone forms depicted in Formula 2, and (e) pharmaceutically acceptable salts thereof.

| FORMULA 1 | FORMULA 2 |
|---|---|
| 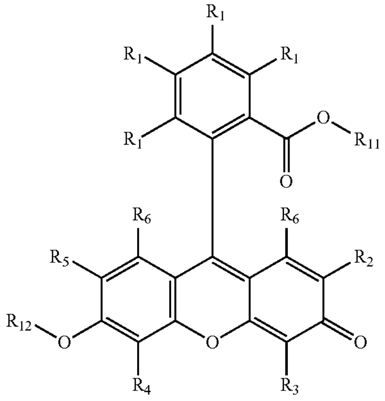 | 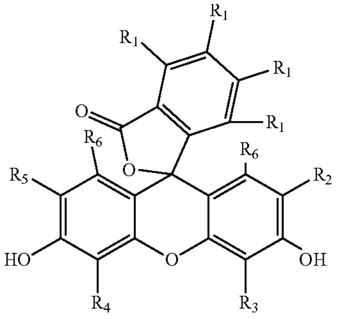 |

A contemplated halogenated xanthene is believed to be more accurately referred to as a halogenated fluorescein inasmuch as fluorescein is a derivative of xanthene. In preferred practice, each $R_1$ of a halogenated fluorescein of Formulas 1 and 2, above, is either a chloro or a bromo substituent, whereas each of $R_2$, $R_3$, $R_4$, and $R_5$ of those formulas is an iodo substituent as are present in Formulas I and II, below. In those formulas below, X is oxygen or nitrogen, "n" is zero or 1 such that when X is Formula I

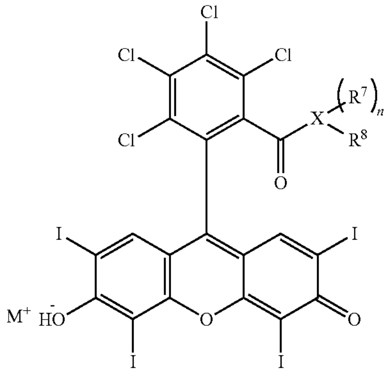

-continued

Formula II

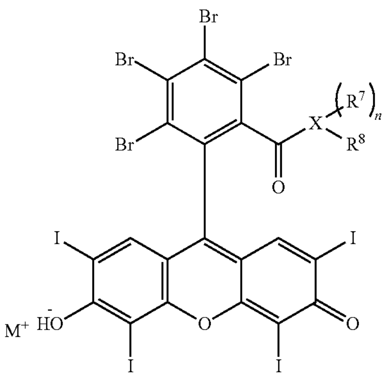

oxygen, n is zero and $R^7$ is absent, whereas when X is nitrogen, n is 1 and $R^7$ is present. When X is oxygen, $R^8$ is selected from the group consisting of hydrogen (H), $M^+$ that is a pharmaceutically acceptable cation, $C_1$-$C_4$ alkyl, and an aromatic ring-containing substituent as defined herein after. When X is nitrogen, $R^7$ and $R^8$ are the same or different and are selected from the group consisting of hydrogen, $C_1$-$C_4$ alkyl, an aromatic ring-containing substituent or together with amido nitrogen atom $R^7$ and $R^8$ form a 5- or 6-membered ring, and an aromatic ring-containing substituent. The aromatic ring-containing substituent is a single ring containing 5- or 6-members, or a 5,6- or 6,6-fused aromatic ring system that contains 0, 1 or 2 hetero ring atoms that are independently nitrogen, oxygen or sulfur.

For ease of description, an aromatic ester or aromatic amide are collectively referred to as an aromatic derivative. As such, those derivatives are formed from an alcohol or amine, preferably monosubstituted, having a single 5- or 6-membered aromatic ring, or a 5,6- or 6,6-fused aromatic ring system that contains 0, 1 or 2 hetero ring atoms that are independently nitrogen, oxygen or sulfur.

Structural formulas of exemplary aromatic ring substituents are set out below:

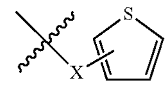,
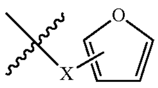,
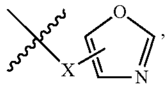,
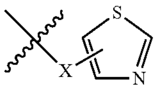,
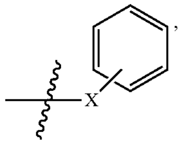,
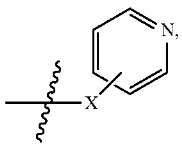
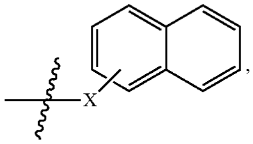,
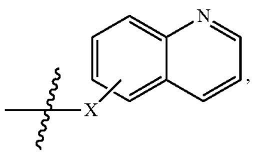,
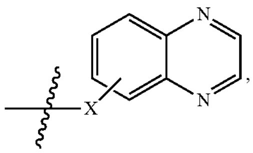,
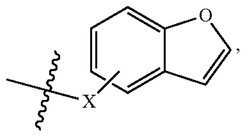, -continued

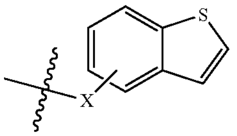
and
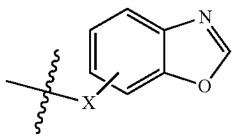

where

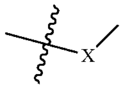

is

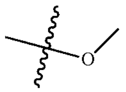 [SMILES: *OC]

or

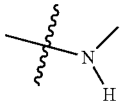

providing an ester or a monosubstituted amide, respectively.

Rose bengal (RB) is a preferred compound for use herein, and its disodium salt, rose bengal disodium (RBD), is the most preferred RB compound. These compounds are used illustratively herein for the group of RB compounds.

The chemical name for rose bengal is 4,5,6,7-tetrachloro-2',4',5',7'-tetraiodofluorescein. A preferred form, rose bengal disodium (PBD), has the following structural Formula Ia:

Ia

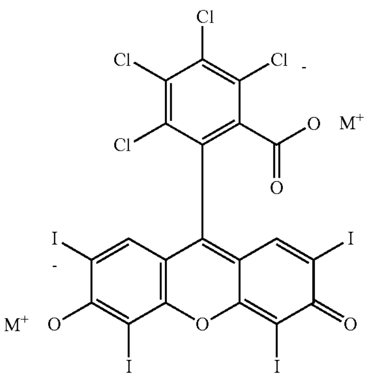

-continued

IIb

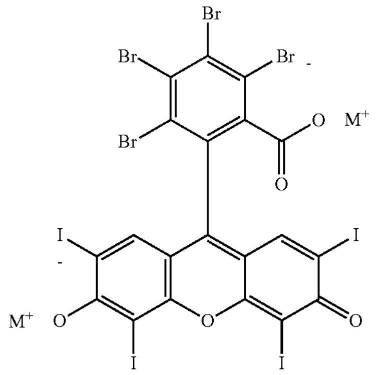

Preparation of highly purified halogenated fluorescein molecules such as rose bengal (Formula Ia above) and the tetra-bromo-tetra-iodo analog (Formula IIb, above) are discussed in U.S. Pat. Nos. 8,530,675, 9,273,022 and 9,422,260. The use of RBD in photochemically-induced treatments is disclosed in U.S. Pat. Nos. 5,998,597, 6,331,286, 6,493,570, 7,390,668 and 8,974,363. Preferably, the cation, $M^+$, in the above structural formulas is sodium ($Na^+$) or potassium ($K^+$).

The terms "physiologically acceptable salt" and "pharmaceutically acceptable salt" in their various grammatical forms refer to any non-toxic cation such as an alkali metal, alkaline earth metal, and ammonium salt commonly used in the pharmaceutical industry, including the sodium, potassium, lithium, calcium, magnesium, barium, ammonium and protamine zinc salts, which can be prepared by methods known in the art. Such salts are usefully prepared by neutralization of an acid form of a contemplated halogenated fluorescein using an alkali metal, alkaline earth metal, or ammonium hydroxide or by admixture with a hydroxide form of an ion exchange resin. A cation halogenated fluorescein salt so formed is preferably soluble in an ultimately formulated topical ophthalmic composition.

A contemplated cation provides a composition-soluble xanthene (fluorescein or fluorescienate) salt. Preferably, the salts are sodium, potassium, calcium and ammonium in either the mono or dibasic salt form. The reader is directed to Berge, *J. Pharm. Sci.* 1977 68(1):1-19 for lists of commonly used physiologically (or pharmaceutically) acceptable acids and bases that form physiologically acceptable salts with pharmaceutical compounds.

A halogenated fluorescein is present in the composition in a keratitis-treating effective concentration. In usual practice, a keratitis-treating effective concentration is about 50 μg/mL to about 3,000 μg/mL, preferably about 100 μg/mL to about 2,000 μg/mL, and more preferably about 500 μg/mL to about 1,500 μg/mL, in the topical ophthalmic composition, measured as DRB.

Thus, if a halogenated fluorescein other than DRB is used, the amount used is based upon the molecular weight of DRB, which is 1017.6 g/Mole. For example, if the four chloro substituents are replaced by four bromo substituents, the molecular weight would be 1195.2 g/Mole. The molecular weight difference is about 17.45 percent. An equivalent amount of the tetra-bromo-tetra-iodo fluorescein to use compared to a given amount of DRB would therefore be about 17.45 percent greater.

A contemplated halogenated fluorescein compound such as rose bengal is dibasic, having $pK_a$ values of 2.52 and 1.81. $pK_a$ value determinations for several contemplated halogenated fluoresceins can be found in Batsitela et al., *Spectrochim Acta Part A* 79(5):889-897 (September 2011).

The pH value of the halogenated xanthene (fluorescein) pharmaceutical composition can be regulated or adjusted by any suitable means known to those of skill in the art. The composition can be buffered or the pH value adjusted by addition of acid or base or the like. As the halogenated xanthenes (fluoresceins), or physiologically acceptable salts thereof, are weak acids, depending upon halogenated xanthene (fluorescein) concentration and/or electrolyte concentration, the pH value of the composition may not require the use of a buffer and/or pH value-modifying agent. It is especially preferred, however, that the composition not be buffered, permitting it to conform to the biological environment, e.g., tear fluid, once administered.

Abelson et al., *Arch Ophthalmol* 99(2):301 (1981) reported measuring the pH value of the tear fluid in the inferior cul-de-sac from 44 normal subjects and found that pH value to be about 6.5 to about 7.7, with a mean value of about 7.0. Thus, a contemplated composition preferably has a pH value of about 6.5 to about 7.6, and preferably about 7.0 to about 7.4.

It is also preferred that the pharmaceutical composition not include any preservatives, many of which can deleteriously interfere with the pharmaceutical composition or formulation thereof, or may complex or otherwise interact with or interfere with the delivery of the halogenated xanthene composition active component. To the extent that a preservative is used, imidurea is a preferred preservative as it does not interact with halogenated xanthenes, either in the pharmaceutical composition or upon administration.

A contemplated treatment method is utilized to treat a mammalian subject in need thereof. A "mammal in need" is a mammal that presents with an eye infection, such as a bacterial, viral, fungal or amoebic infection. Such infections tend to usually be a bacterial infection, and the infecting bacteria are typically Gram-positive bacteria.

Illustrative treated Gram-positive bacteria include one or more of drug-susceptible and drug-resistant *S. aureus, S. epidermis, E. faecalis* and *E. faecium*, as well as one or more of *Bacillus subtilis, Bacillus cereus*, and *Streptococcus salivarius*. Gram-positive bacteria are present within or on mammalian cells of the eye when an infected eye is treated (the cells are contacted).

Some Gram-positive bacterial strains are referred to herein as being "resistant" or "drug resistant" or other grammatical variants of resistance. The "resistance" meant here is of the bacteria to treatment with one or more antibacterial pharmaceutical products that are usually deemed to be bactericidal at known concentrations and bacterial cell densities to that type of bacteria. There are thus, both "drug-susceptible" and "drug-resistant" strains of bacteria such as *Staphylococcus aureus* (*S. aureus*), *Staphylococcus epidermidis* (*S. epidermis*), *Enterococcus faecalis* (*E. faecalis*), and *Enterococcus faecium* (*E. faecium*). Illustrative drugs to which several common bacteria strains have become resistant include vancomycin, methicillin and gentamicin.

A similar method is also contemplated for treating Gram-negative bacteria that is preferably one or more of *Burkholderia, Salmonella*, and *Proteus*. Here, an above RB compound is present dissolved or dispersed in an aqueous pharmaceutical composition at a concentration of about 10 μg/mL to about 100 μg/mL, and preferably at about 20 μg/mL to about 50 μg/mL.

As used herein, the word "administration" is used to mean the beginning of a treatment regimen in which the composition is applied to the outer surface of the infected eye. Thus, administration typically entails placing a dose of an ophthalmic composition described herein onto the surface of the eye or into the pocket or pouch formed by pulling down the lower eyelid, and then closing the eyelid to distribute the ophthalmic composition over the external surface of the treated eyeball.

The Treatment Method

A contemplated treatment method comprises contacting the corneal surface of the subject in need with a composition containing an anti-Gram-positive bacterial amount of a halogenated fluorescein compound. Using rose bengal as illustrative of such compounds, an anti-Gram-positive bactericidal effective amount of RB is administered to the mammalian subject in need and can be formulated using a thickened aqueous liquid, gel, or other formats as discussed previously.

The treated eye is thereafter maintained in the substantial absence of actinic light for a time period of about 3 to about 12 hours. Thus, for example, after application, the eye lid is closed, a light-blocking patch is placed over the treated eye, ambient light is shut off, or the like. Perhaps most easily, the eye is treated just prior to the recipient retiring to sleep for the evening.

In one embodiment, the Gram-positive bacterial cells are present on or in (e.g., infecting) a subject mammal. Illustratively, a subject mammal can have a dermatological Gram-positive bacterial infection such as that of *Streptococcus pyogenes*, or particularly in the case of a topical treatment of an open wound, as a treatment for a present infection and as a preventative from subsequent Gram-positive bacterial infection.

A treated subject mammal can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Each contemplated composition administration is typically repeated until the treated bacterial disease (infection) is diminished to a desired extent, such as not being detectable. Thus, the administration to a mammalian subject in need can occur a plurality of times within one day, daily, weekly, monthly or over a period of several months to several years as directed by the treating physician.

As directed by medical personnel involved with a treatment, the corneal epithelium in an area surrounding the infection, e.g. a corneal ulcer, can be debrided prior to administration of a contemplated composition to obtain a de-epithelized area to increase rose bengal absorption.

Results

Pharmaceutical Grade of Rose Bengal (RB)

Provectus Biopharmaceuticals, Inc. of Knoxville, TN, (Provectus) used commercial-grade RB and sought a manufacturing process to prepare a pure form of RB as a drug substance. However, several challenges in the purification of RB were found due to commercial-grade reactions occurring during the dye manufacturing process, and the other by-products which lost one or more of the iodide substituents.

It was concluded that commercial-grade RB is not capable of efficiently yielding a pharmaceutical-grade material in sufficient quantity to support clinical development and registration by the FDA and other global drug regulatory agencies. A novel multi-step approach for synthesizing and manufacturing RB was established by Provectus [Singer et al., U.S. Pat. Nos. 8,530,675, 9,273,022 and 9,422,260. A key element of that work was the ability to eliminate the conditions that lead to the formation of the key historical impurities.

Those synthesis and purification methods have been applied to a good manufacturing practice (GMP), producing RB with a pharmaceutical grade. This RB, PV-10®, is sterile 10% solution of rose bengal disodium (RBD) in 0.9% aqueous saline available from Provectus that is manufactured under the guidelines of The International Council for Harmonization of Technical Requirements for Pharmaceuticals for Human Use (ICH), and designed to apply as an injectable pharmaceutical. The pharmaceutical grade RBD is also present in a differently-formulated topical medication [U.S. Pat. No. 9,422,260; Innamarato et al., *BMC Cancer* 21:756 (2021); Thompson et al., *Melanoma Res.* 31:232-241 (2021); and Swift et al., *Onco Targets Ther.* 12:1293-1307 (2019)] referred to as PH-10®. Both preparations utilize rose bengal disodium (RBD), whose structural formula was shown previously, as the active ingredient. Because many soluble salts of rose bengal can be utilized in addition to the disodium salt, "RB" is used herein as the designation for any pharmaceutically acceptable salt of rose bengal, whereas the designation "RBD" refers specifically to rose bengal disodium.

Microorganisms

The microbial source of infection can bacterial, viral, fungal or amoebic. In usual practice, the source of infection is bacterial, and an infecting bacterium is preferably a Gram-positive bacterium.

The antibacterial activity of RB via photodynamic approaches has been studied in several research groups [See, Kurosu et al., *Molecules* 27:322 (2022) and the citations therein]. Applications of photodynamic therapy of RB are not limited to skin infections, including cellulitis, erysipelas, impetigo, folliculitis, and furuncles and carbuncles. However, spectrum of activity, rate of killing, and biofilm eradication activity of RB have been reported sporadically.

The bactericidal activity of pharmaceutical-grade of RB against a battery of microbes including Gram-positive, Gram-negative aerobic bacteria, including *Mycobacterium* spp. Under different light sources (fluorescence, LED, and sun light) and in a dark condition has been reinvestigated by Kurosu et al., above. Interestingly, although the irradiation with actinic light exhibited greater immediate potency, RB also exhibited anti-bacterial activity in the dark.

The present invention utilizes that anti-bacterial activity in the darkness in the present invention. Thus, the mammalian subject in need of treatment, such as a human with a bacterial eye infection, applies an anti-bacterial effective amount of a contemplated pharmaceutical composition within zero to about five minutes before retiring and closing her/his/their eyes.

Minimum inhibitory concentrations (MICs, in μg/mL) obtained via broth dilution and agar dilution methods for a time period of 24 hours (h) in a dark room, using 96-well plates covered with aluminum foil from the dark condition of the above Kurosu et al. paper are summarized in Table 1, below. RB used in Table 1 is a diluted form of PV-10® that was provided by Provectus Biopharmaceuticals, Inc. (Knoxville, TN, USA) [Singer et al., U.S. Pat. Nos. 8,530,675, 9,273,022 and 9,422,260.].

TABLE 1

MIC of a series of fungus, Gram-positive and Gram-negative bacteria via broth dilution method

| Entry Number | Microbe | MIC (μg/mL) |
|---|---|---|
| 1 | *Bacillus subtilis* ATCC6051 | 50 |
| 2 | *Bacillus cereus* NRRL B-569 | 50 |
| 3 | *Bacillus cereus* 13061 ™ | 50 |
| 4 | *Staphylococcus aureus* 6538 ™ | 50.0 |
| 5 | *Staphylococcus aureus* subsp. *Aureus* BAA-1683 (a MRSA strain) | 50 |
| 6 | *Staphylococcus aureus* subsp. *Aureus* BAA-41 ™ (a MRSA strain) | 25.0 |
| 7 | *Staphylococcus aureus* subsp. *Aureus* BAA-42 ™ (a MRSA strain) | 50.0 |
| 8 | *Staphylococcus aureus* subsp. *Aureus* BAA-44 ™ (a MRSA strain) | 50.0 |
| 9 | *Staphylococcus aureus* subsp. *Aureus* BAA-2094 ™ (a MRSA strain) | 25.0 |
| 10 | *Staphylococcus aureus* BAA-2313 ™ (a MRSA strain) | 25.0 |
| 11 | *Staphylococcus aureus* subsp. *Aureus* 33592 ™ (a methicillin and gentamicin resistant strain) | 50.0 |
| 12 | *Staphylococcus aureus* AIS2006032 (a vancomycin-resistant strain) | 50.0 |
| 13 | *Staphylococcus aureus* BR 5 (A methicillin and vancomycin resistant strain) | 25.0 |
| 14 | *Staphylococcus aureus* strain AIS 1000505 (VRS10, a vancomycin-resistant strain) | 25.0 |
| 15 | *Staphylococcus aureus* USA100 strains 71080 (VRS8, a vancomycin-resistant strain) | 25.0 |
| 16 | *Staphylococcus epidermidis* 35984 ™ | 25.0 |
| 17 | *Enterococcus faecalis* 19433 ™ | 25.0 |
| 18 | *Enterococcus faecium* 349 ™ | 50.0 |
| 19 | *Enterococcus faecium* BAA-2320 | 25.0 |
| 20 | *Enterococcus faecium* NR-32065 (a vancomycin- resistant strain) | 50.0 |
| 21 | *Enterococcus faecium* patient #3-1, NR-31912 (a vancomycin-resistant strain) | 50 |
| 22 | *Enterococcus faecium* UAA714 (a vancomycin-resistant strain) | 50 |
| 23 | *Streptococcus salivarius* subsp. *Salivarius* 7073 ™ | 25.0 |
| 24 | *Streptococcus pneumoniae* 6301 ™ | >100 |
| 25 | *Mycobacterium smagmatis* 607 ™ | 25.0 |
| 26 | *Mycobacterium avium* subsp. *Avium* 2285 | 50.0 |
| 27 | *Mycobacterium kansasii* 824 ™ | 50.0 |
| 28 | *Mycobacterium bovis* 35734 ™ (BCG) | 50.0 |
| 29 | *Mycobacteroides abscessus* 19977 ™ | 50.0 |
| 30 | *Saccharomyces cerevisiae* BY4743 | 125 |

RB's bactericidal activity was examined against a panel of 7 methicillin-resistant *S. aureus* (MRSA) with different SCCmec types (entries 5-11) of Table 1 [Zuo et al., *Sci. Rep.* 11:Article 5447 (2021)]. All MRSA strains tested in Table 1 were killed by RB at 0.78-3.1 μg/mL concentrations under the fluorescent or LED light. RB was further examined against 4 vancomycin-resistant *S. aureus* strains (entries 12-16); all vancomycin-resistant strains were killed at below 1.0 μg/mL concentrations under either lighting condition.

*Staphylococcus epidermidis* is an anaerobic bacterium, but grows well under aerobic conditions. It was effectively killed by RB under an aerobic condition (entry 16). Drug-susceptible and drug-resistant *Enterococcus faecalis* including vancomycin-resistant strains were killed by RB (entries 17-21). *Streptococcus salivarius* was susceptible to RB (entry 23), whereas *Streptococcus pneumoniae* showed resistance to RB (entry 24). The basis for that resistance is presently unknown.

Thus, under the dark condition, RB showed antibacterial activity against all Gram-positive bacteria listed in entries 1-23 (Table 1) at 25.0-100 μg/mL concentrations. Under the dark condition RB is known to display antibacterial activity at high concentrations. All Gram-negative bacteria assayed in Table 1 were not susceptible to RB under the dark condition. These data support the idea that RB has one or more unknown mechanisms to inhibit the growth of bacteria other than via the excitation mechanism of triplet oxygen, generating cytotoxic reactive oxygen species.

Antibacterial activity of RB against 5 *Mycobacterium* spp. Was examined (entries 25-29). Interestingly, under the dark condition, these Mycobacteria were killed at similar MIC to those observed under illumination conditions. RB inhibited growth of *Saccharomyces cerevisiae* at higher concentrations than the bacteria under the dark condition (entry 30).

The MIC values of RB determined by the agar dilution method differed from those determined by the broth dilution method (Table 1). Selected examples of the MIC values determined by the agar dilution method are summarized in Table 2 shown by renumbering the assayed microbes.

TABLE 2

MIC of a series of Gram-positive bacteria and Mycobacteria via agar dilution method

| Entry Number | Microbe | MIC (μg/mL) |
|---|---|---|
| 1 | *Bacillus subtilis* ATCC6051 | 125 |
| 2 | *Bacillus cereus* 13061 ™ | 125 |
| 3 | *Staphylococcus aureus* 6538 ™ | 25.0 |
| 1 | *Staphylococcus aureus* subsp. *Aureus* BAA-44 ™ (a MRSA strain) | 50.0 |
| 5 | *Mycobacterium smegmatis* 607 ™ | 50.0 |

The growth of Gram-positive bacteria such as *B. subtilis, B. cereus*, and *S. aureus* were inhibited at about 25 to about 125 μg/mL concentrations (entries 1-4 in Table 2), which are greater than the MIC values determined by the broth dilution method. *M. smegmatis* (ATCC607™) was killed at lower concentration on the drug-containing agar plates (or wells) than in those in broth (entry 29, Table 1; entry 5, Table 2) [Lelovic et al., *J.* Antibiot 73:780-789 (2020)].

Under the dark condition, the MICs of RB determined via the agar dilution method displayed good agreement with the values measured in the broth dilution method. Minimum bactericidal concentrations (MBCs) of RB against the selected bacteria are also summarized in Table 2, above.

Exemplary Gram-positive bacteria for treatment and killing include one or more of drug-susceptible and drug-resistant *S. aureus, S. epidermis, E. faecalis* and *E. faecium*, as are one or more *Bacillus subtilis, Bacillus cereus*, and *Streptococcus salivarius.*

Anti-Biofilm Activity of Pharmaceutical Grade RB (HP-RBf)

The antibacterial character of RB observed in the previous section encouraged evaluation of antibiofilm efficacy of RB in Gram-positive bacteria. The data summarized above indicate that RB possesses a significant drug affinity or permeability onto (or into) Gram-positive bacteria.

Antimicrobial and antifungal photodynamic therapy have been studied with the photosensitizers under biofilm conditions; however, a limited number of bacterial biofilms have been examined with RB [Pérez-Laguna et al., *Photodiagnosis Photodyn. Ther.* 21:211-216 (2018)].

Here, efficacy of RB against biofilms of a drug-susceptible *S. aureus* 6508™, drug-resistant *S. aureus* 71080 (VRS8) and *E. faecium* NR-32065 was studied under florescent light and dark conditions. Linezolid is not an effective drug in eradicating biofilms of Gram-positive bacteria, but has a beneficial effect in prevention of biofilm formations [Reiter et al., *J. Med. Microbiol.* 62:394-399 (2013)], and was used as a control.

Linezolid was applied as a positive control at very high concentration of 600 μg/mL (>100×MIC for the planktonic cells) in biofilm assays reported by Kurosu et al., *Molecules* 27:322 (2022). Those authors reported that they confirmed that all strains tested form strong biofilms on the polystyrene well plates. Under the fluorescent light, RB could eradicate the biofilms of *S. aureus* 6508™ with a 7-log reduction at 30.0 μg/mL (38×MIC) concentration, which demonstrated the same level of efficacy as observed for linezolid (at 600 μg/mL) (Kurosu et al., above, FIG. 3).

RB showed a biofilm eradication activity in a dose-dependent manner in both the under light and in the dark conditions. Although requiring higher concentrations, RB showed a biofilm eradication activity under the dark condition. At 50.0 μg/mL (2×MIC under dark) concentration, RB significantly reduced the number of viable bacteria. At 500 μg/mL (20×MIC) concentration, only about 110 to about 150 CFU/mL were observed. No viable bacteria (N.D.) were appeared at 1,000 μg/mL concentration. Similar trends were observed in the biofilms of the drug-resistant *S. aureus* 71080 (VRS8) and *E. faecium* NR-32065 with much lower RB concentrations.

Antibacterial Mechanisms of RB

Antibacterial photodynamic therapy of RB has been reported in several articles. Permeation of RB through bacterial cell walls and binding to cell membranes followed by production of reactive oxygen species are likely bactericidal mechanisms in illumination conditions [Nsubuga et al., *Nanoscale Adv.* 3:1375 (2021); and Lambert et al., *Photochem. Photobiol.* 66:15-25 (1997)]. Although relatively high concentrations are required, RB kills a majority of Gram-positive bacteria including *Mycobacterium* spp. In dark conditions. It also effectively eradicates biofilms of Gram-positive bacteria (above). Antibacterial activity of RB in dark conditions remains far from completely understood [Nakonechny et al., *Int. J. Mol. Sci.* 29:3196 (2019); and Kim et al., *J. Enzyme. Inhibit. Med. Chem.* 35:1414-1421 (2020)].

RB kills Mycobacterial spp. At 12.5-25.0 mg/mL in illumination conditions, and at 25.0-50.0 mg/mL in dark conditions (Table 1). In both conditions, RB kills five Mycobacterial spp. At a slower rate than that of Gram-positive bacteria. RB seems to have low-permeability of mycobacterial cell walls. Due to rapid bactericidal effect of RB against Gram-positive bacteria even in the dark condition, generation of RB-resistant mutants of Gram-positive bacteria is an extremely difficult task.

We successfully generated RB-resistant mutants of *M. smegmatis*, which had the MIC value of 200 mg/mL [Lelovic et al., *J. Antibiot.* 73:780-789 (2020)]. The RB-resistant strain was susceptible to most of TB drugs [amikacin, capreomycin, rifampicin, aminouridyl phenoxypiperidinylbenzyl butanamide (APPB), and ethionamide](Table 3, below).

TABLE 3

MICs of RB and anti-mycobacterial agents against *M. smegmatis* and its PV-10-resistant strain[a]

| Drug | MIC (μg/mL) against *M. smegmatis* 607 ™ (wild-type) | MIC (μg/mL) against *M. smegmatis* 607 ™ (RB mutant) |
|---|---|---|
| Rose Bengal | 12.5 | 200 |
| Isoniazid (INH)[b] | 1.56 | 25-50 |
| Ethionamide (ETH) | 12.5 | 12.5 |
| Amikacin | 0.78 | 0.78 |
| Capreomycin | 3.13 | 3.13 |
| Rifampicin | 1.56 | 1.56 |
| APPB | 0.20 | 0.20 |

[a]The MIC values were determined in dark condition. All studies were triplicated.
[b]An inhibitor of mycolic acid synthesis.
[c]APPB = aminouridyl phenoxypiperidinylbenzyl butanamide, a MraY/WecA inhibitor.

However, it showed a cross-resistance to Isoniazid (INH). INH is a prodrug that requires oxidative activation by the enzyme KatG, which belongs to catalase-peroxidase families. KatG oxidizes INH to form an electrophilic species, an isonicotinoyl radical molecule, which reacts with the NADH-dependent enoyl-ACP (acyl carrier protein) reductase, an enzyme involved in the biosynthesis of mycolic acids of mycobacteria (Scheme 1, below) [Vilchèze et al., *Microbiol. Spectr.* 2: MGM2-0014-2013 (2014); and Morlock et al., *Antimicrob. Agents Chemother* 47:3799-3805 (2003)].

Scheme 1

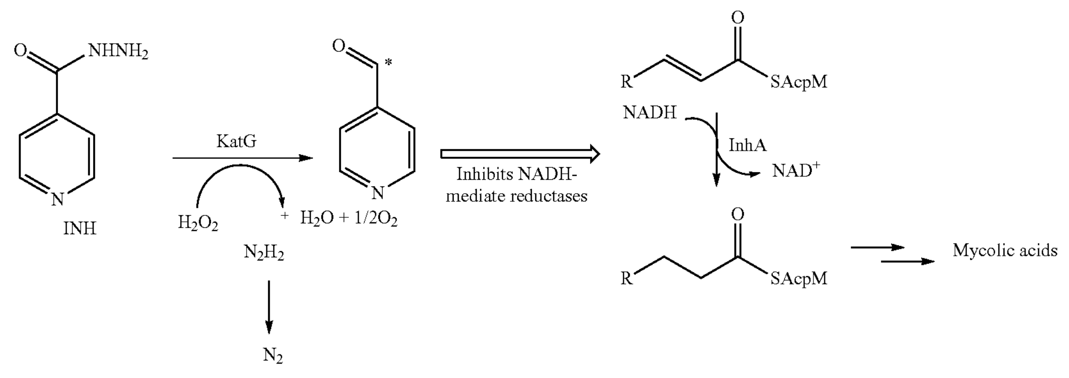

The RB-resistant *M. smegmatis* strain acquired medium-INH resistance but did not show resistance to ethionamide (ETH). The major mechanism of INH resistance is mutation in katG, while ETH is activated by the monooxygenase EthA [Laborde et al., *Org. Biomol. Chem.* 14:8848-8858 (2016)]. These observations may imply that the RB's antibacterial mechanisms share one or more INH metabolic enzymes to form bactericidal species.

To elucidate a potential mechanism of action, a whole-genome sequencing analysis of an RB-resistant *M. smegmatis* ATCC607 strain was performed using the next-generation of DNA sequencing technologies [Lei et al., *Microbiol. Resour. Announc.* 8:e00551 (2019)]. One identified insertion mutation occurred in anti-sigma E factor gene (rseA: evidenced TG:104 vs. T:0) and aquaporin family protein gene (evidenced GCACCCT:71 vs. G:0), respectively.

Consequently, these insertion mutations caused the reading frame changes in the corresponding proteins and generated the truncated proteins compared to its parental strain. in Streptococcal spp. [Tong et al., *J. Biol. Chem.* 294:4583-4595 (2019)]. Therefore, we hypothesize that RB may inhibit the aquaporin function, leading to accumulation of $H_2O_2$ within the bacterial cells. Interestingly, a single nucleotide deletion causing the frameshift mutation was observed in molybdopterin-dependent oxidoreductase (evidenced T:74 vs. TC:0) of the RB-resistant strain.

The oxidoreductase systems can form superoxide by reduction of molecular oxygen or NO by reduction of inorganic nitrate. RB may serve as a single-electron acceptor in the redox of the oxidoreductases that will produce the radical anion ($RB^{\bullet}$-) or RB triplet state, undergoing electron-transfer reaction with oxygen. As such, the involvement of molybdopterin-dependent oxidoreductase is proposed in the generation of reactive oxygen or nitrogen spp. through the excitation of RB under dark conditions (Scheme 2, below). The oxidoreductase in Scheme 2 is molybdopterin-dependent oxidoreductase xanthine dehydrogenase family protein. The "·OH+OH⁻" in Scheme 2 is a reactive oxygen species (ROS) or a reactive nitrogen species.

Scheme 2

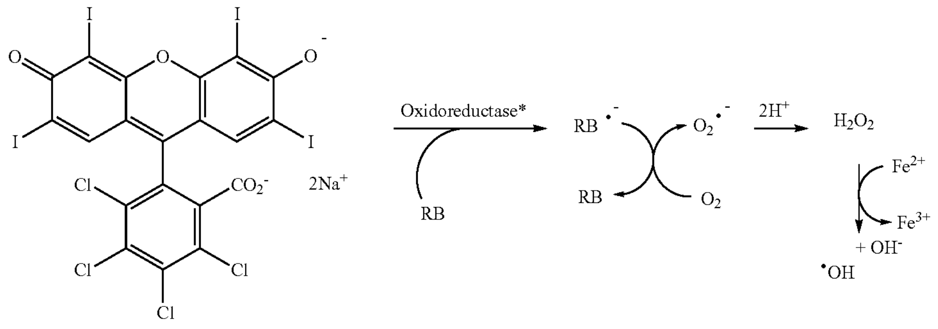

It has been reported that RseA functions as a specific anti-sigma E factor in *Mycobacterium tuberculosis* and that the sigma E factor (SigE) enables the mycobacterial organisms to tolerate a variety of stress responses [Boldrin et al., *Sci. Rep.* 9:17643 (2019); and Wu et al., *J. Bacteriol.* 179:2922-2929 (1997)]. Thus, the expression of a non-functional RseA in the RB-resistant mutant may affect the activity of SigE, increasing the bacterial tolerance to RB. On the other hand, the aquaporin family proteins exist in various organisms and play a critical role in bidirectional flux of water and uncharged solutes cross cell membranes.

It was reported that a null mutation of the Streptococcal aquaporin homolog increased the intracellular $H_2O_2$ retention, indicating that aquaporin mediates transporting $H_2O_2$ The KatG gene was intact in the RB-resistant strain. Thus, it remains difficult to speculate a mechanism that confers the cross-resistance with INH. However, mutations in several transcriptional regulators of the RB-resistant strain were observed that may affect the expression level of KatG, suppressing the INH-activation. It generates hydroxy radicals (reactive oxygen species) through the Fenton reaction of $H_2O_2$. Requirement of relatively high concentration of RB to display bactericidal activity against Gram-positive bacteria including Mycobacterial spp. may imply that affinity of RB with catalases is moderate. Similarly, a cytotoxicity mechanism of RB in mammalian cells may be explained. As shown in Scheme 3, below.

Scheme 3

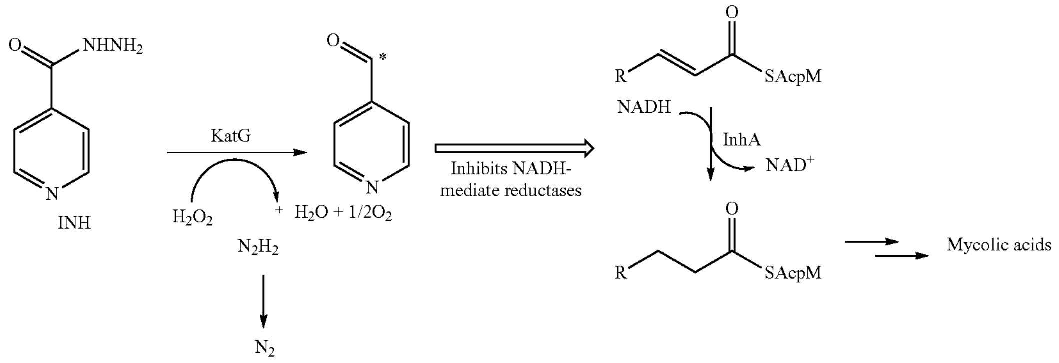

RB has been used for over 50 years to diagnose eye and liver disorders. It is often useful as a stain in diagnosing certain medical issues, such as conjunctival and lid disorders (vide supra). In these applications, 0.1-2.0% RB (i.e., 1,000-20,000 μg/mL) has been used.

RB in concentrations below 2.0% are considered to be safe under natural and artificial lights [Whitcher et al., *Am. J. Ophthalmol.* 149:405-415 (2010)]. A healthy cell line, Vero (the kidney of an African green monkey) cells was chosen to determine in vitro cytotoxicity of RB under the fluorescent light.

Large data sets of cytotoxicity of antibacterial and anticancer agents against Vero cells have been generated, which allow comparison of the toxicity level of new molecules [Siricilla et al., *J. Med. Chem.* 60:2869-2878 (2017); and Siricilla et al., *J. Antibiot.* 68:271-278 (2015)]. In a 24 h study under the dark, RB showed the $IC_{50}$ value of 300 μM (292 μg/mL) against Vero cells.

Therapeutic concentrations of RB are likely to be about 0.1 μM to about 10 μM. Thus, these in vitro cytotoxicity tests imply that skin infections can be treated with RB without causing cytotoxicity of host cells under illumination conditions.

CONCLUSIONS

Provectus has established a manufacturing and purification process for pharmaceutical-grade RB that fulfills both cGMP and ICH requirements. We have evaluated the antibacterial activity and cytotoxicity of a pharmaceutical-grade RB formulated product (PV-10®) as an exemplary RB compound in illuminating and dark conditions. The comprehensive MIC data for RB via saline-diluted PV-10® summarized here indicate that RB is very effective in killing most Gram-positive bacteria (MIC 0.39-3.1 μg/mL), except *Streptococcus pneumoniae* sp.

*S. pneumonia* is one of very few Gram-positive bacteria that is susceptible to colistin (polymixin E), an anti-Gram-negative drug. We have studied the relationship between RB's bactericidal effect and colistin-resistance in both Gram-positive and -negative bacteria. The resistance mechanism of *S. pneumoniae* against RB will be reported elsewhere.

We confirm that RB is an excellent agent to eradicate biofilms of Gram-positive bacteria, including drug-resistant strains. Under fluorescent and dark conditions, RB significantly reduced a number of viable cells of the drug-resistant strains of *S. aureus* and *E. faecium* in a concentration-dependent manner. These studies indicate that RB has the potential antibacterial agent to kill drug-resistant bacteria in any growth phases.

Materials and Methods

Antibiotics

All antibiotics were purchased from commercial sources [amikacin disulfate salt (Sigma Aldrich, A1774-1G), capreomycin sulfate (Sigma Aldrich, C4142-1G), ciprofloxacin hydrochloride monohydrate (TCI, C2227), ethionamide (TCI, E0695), isoniazid (Sigma Aldrich, I3377-5G), linezolid (Chem-Impex, 29723), meropenem trihydrate (Ark Pharm, AK161987), rifampicin (Sigma Aldrich, R3501-1G)] and used without further purification unless otherwise noted. APPB (aminouridylphenoxypiperi-dinylbenzyl butanamide) was synthesized according to the reported procedure. [Mitachi et al., *ACS Omega* 2018, 3:1726-1739; and Mitachi et al., *MethodsX* 2019, 6:2305-2321.]

Formulation of Pharmacological Grade Rose Bengal in Saline (PV-10®).

Rose bengal disodium salt was synthesized according to Provectus' proprietary procedure. The detailed procedure was as described in U.S. Pat. Nos. 8,530,675, 9,273,022 and 9,422,260.

Acquisition of Bacteria

The drug susceptible bacteria and yeasts used in this program were purchased from ATCC (The American Type Culture Collection, Manassas, VA). The drug-resistant strains were acquired from BEI Resources (NIAID).

Log Phase Bacterial Culture

All liquid bacterial culturing was performed with a conical flask with an air filter. A single colony of a bacterial strain was grown according to the conditions recommended by ATCC. Seed cultures and larger cultures of bacteria were obtained using media recommended by ATCC. *M. smegmatis* (ATCC 607) was cultured on a 0.5% Tween® 80 Middlebrook 7H10 nutrient agar (0.4% glycerol) [46]. The culture flasks were incubated for 3-4 days for *M. smegmatis* (ATCC 607), and for 10-12 days for *M. tuberculosis* $H_{37}Rv$ in a shaking incubator at 37° C. with a shaking speed of 200 rpm and cultured to mid-log phase (optical density—0.5). The optical density was monitored at 600 nm using a 96 well microplate reader.

MIC Assays

All testing follows the guidelines set by the Clinical & Laboratory Standards Institute (CLSI) ["Determining laboratory reference intervals: CLSI guideline makes the task manageable," *Lab. Med.* 40:75-76 (2009).]. Minimum inhibitory concentrations (MICs) were determined by broth dilution microplate alamar blue assay or by OD measurement. All compounds were stored in DMSO or saline (1 mg/100 μL concentration). This concentration was used as the stock solution for all MIC studies. Each compound from stock solution was placed in the first well of a sterile 96 well plate and a serial dilution was conducted with the culturing broth (total volume of 10 μL). The bacterial suspension at log phase (190 μL) was added to each well (total volume of 200 μL), and was incubated for 24 h at 37° C. 20 μL of resazurin (0.02%) was added to each well and incubated for 4 h, (National Committee for Clinical Laboratory Standards (NCCLS) method (pink=growth, blue=no visible growth)). The OD measurements were performed for all experiments prior to performing colorimetric assays. The absorbance of each well was also measured at 570 and 600 nm via UV-Vis.

Minimal Bactericidal Concentration (MBC) Assays

A single colony of a specific bacterium (grown on an agar plate) was inoculated into the culture broth. A bacterial culture was grown overnight (about 18 hours), then diluted in growth-supporting broth to a concentration between $1\times10^3$ and $1\times10^9$ CFU/mL. Based on the MIC values, agar plates containing a drug (MIC, 2×-20×MIC) were prepared. A series of drug-containing agar plates were inoculated with equal volumes of the specific bacterium. The agar plates were incubated at the appropriate temperature and duration. CFU/mL were counted. The MBC values were determined by reduction of >99.9% of bacteria.

Mammalian Cell Lines and Culturing

Vero cells (ATCC™ CCL-81) were purchased from the ATCC. HEK cells (SCCE020) were purchased from MilliporeSigma. The cell lines were cultured and maintained in the media as recommended by the suppliers.

Vero cells were cultured in Eagle's Minimum Essential Medium (MEM) (CORNING®, 10-009-CV) supplemented with 10% FBS, 1% Penicillin-Streptomycin Solution (Cellgro®, 30-002-CI), 1% HyClone™ MEM Non-Essential Amino Acids Solution (100×) (GE Healthcare Life Sciences, SH30238.01) and 1% HyClone™ Sodium Pyruvate 100 mM Solution, (GE Healthcare Life Sciences, SH30239.01) and incubated in a 37° C. incubator with 100% humidity and 5% $CO_2$. Cultures were refreshed with fresh medium every 2 days until the culture reaches 100% confluence, which takes approximately 5 days depending on the proliferation rate.

Human Epidermal Keratinocytes, Neonatal (MILLIPORE®, Catalog #SCCE020) were cultured in EpiGRO™ Human Epidermal Keratinocyte Complete Culture Media Kit (MILLIPORE®, SCMK001) and incubated in a 37° C. incubator with 100% humidity and 5% $CO_2$. Refresh with fresh medium after 2 days and three times weekly until the culture reaches 100% confluence.

Cytotoxicity Assay with Vero Cells

All testing follows the guidelines set by the Clinical & Laboratory Standards Institute (CLSI) with minor modifications. Cytotoxicity assays for PV-10 were performed in a 24-well plate. Into each well (1 mL medium/well), 1 μL of drug concentration was added. After 1, 2, 3 and 4 h of incubation under the light at room temperature (r.t.), the medium was removed, and the cells were washed with PBS (×3). After adding the medium (1 mL/well), 10 μL of 3-(4,5-dimethylthiazol-2-yl)-2,5-diphenyltetrazolium bromide (MTT) solution (5 mg/mL in PBS) was added and incubated for another 3 h at 37° C. (5% $CO_2$). The medium was removed, and DMSO (1 mL/well) was added. Viability was assessed on the basis of cellular conversion of MTT into a purple formazan product. The absorbance of the colored formazan product was measured at 570 nm by a BioTek Synergy™ HT Spectrophotometer [Mitachi et al., *J. Med. Chem.* 63:10855-10878 (2020)].

Vero cells [$5\times10^4$ cells/well (in 196 μL of the culture medium)] were plated in a 96-well plate and the cell cultures were incubated for 4 days to form the monolayer (100% confluence). Into each well RB (0-300 mM) was added.

Images were obtained every hour using an IncuCyte® Live-Cell Imaging System (Essen BioScience, Ann Arbor, MI). Cell proliferation was quantified using the metric phase object confluence (POC), a measurement of the area of the field of view that is covered by cells, which is calculated Whole-Genome Sequencing of *M. smegmatis* Strains RB-resistant *M. smegmatis* (ATCC607™) strains were prepared according to the procedures reported previously [Kaser et al., *Cold Spring Harb Protoc.* (2010)]. To identify single nucleotide polymorphisms (SNPs) that may contribute to the bacterial resistance to RB, the genomic DNAs were purified from the stationary cultures of RB-resistant mutant and its parental control *M. smegmatis* 607™ according to the procedure reported previously [Lelovic et al., *J. Antibiot.* 73:780-789 (2020)].

The purified genomic DNA was submitted to the University of Minnesota Genomic Center (UMGC) for quality control analysis, the library preparation and DNA sequencing using an advanced Illumina MiSeq™ DNA-seq technology. Sequence reads from the mutant and the control were evaluated for their quality using FastQC. Low quality tails and adapters were removed with Trimmomatic [Lei et al., *Methods Mol. Biol.* 2069:125-138 (2020)]. The whole-genome sequence of *M. smegmatis* strain FDAARGOS_679 was used as a reference, and SNPs or other variants such as deletion and insertions were called by using a bioinformatic tool Snippy [https://github.com/tseemann/snippy].

Each of the patents, patent applications and articles cited herein is incorporated by reference. The articles "a" and "an" are used herein to refer to one or to more than one (i.e., to at least one) of the grammatical object of the article.

The foregoing description and the examples are intended as illustrative and are not to be taken as limiting. Still other variations within the spirit and scope of this invention are possible and will readily present themselves to those skilled in the art.

The invention claimed is:

1. A method of treating a mammalian subject having a Gram-positive bacterially-infected eye that exhibits keratitis consisting of the steps of treating said Gram-positive bacterially-infected eye by administering to that microbially-infected eye a keratitis-treating effective amount of an ophthalmic composition containing a halogenated fluorescein or pharmaceutically acceptable salt, amide or ester thereof dissolved or dispersed in an aqueous ophthalmic carrier and present in a bacterial keratitis-treating effective concentration of about 0.2 μg/mL to about 50 μg/mL in the composition, said ophthalmic composition having a pH value of about 6.5 to about 7.6, a viscosity of about 10 to about 300 cps and an osmolality of about 270 mOsm/kg to about 340 mOsm/kg, and maintaining said treated eye in the substantial absence of actinic light for a time period of about 3 to about 12 hours so that said treatment is carried out in the substantial absence of actinic light.

2. The method according to claim 1, wherein said ophthalmic composition is maintained in a vessel opaque to actinic light prior to said administration.

3. The method according to claim 1, wherein said halogenated fluorescein or pharmaceutically acceptable salt or ester thereof has the chemical formula of one or both of FORMULA 1 and/or FORMULA 2

FORMULA 1

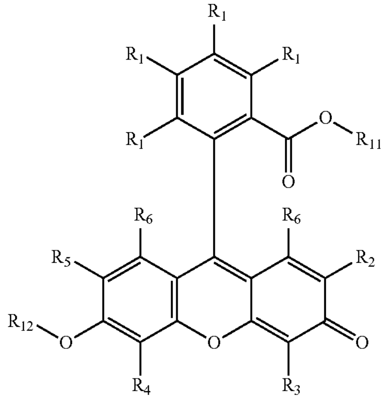

FORMULA 2

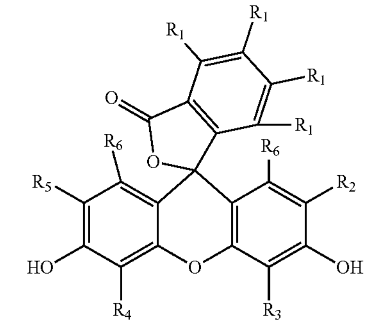

wherein $R_1$ is independently F, Cl, Br, I, H or $C_1$-$C_4$ alkyl;

$R_2$, $R_3$, $R_4$, and $R_5$ are independently Cl, H or I with at least one substituent selected from $R_2$, $R_3$, $R_4$, $R_5$ being I; and $R_6$ is independently H or $C_1$-$C_4$ alkyl; $R^{11}$ is H or $C_1$-$C_4$ alkyl; $R^{12}$ is H or $C_1$-$C_7$ acyl; and all (a) tautomeric forms; (b) atropisomers, (d) enantiomers of lactone forms depicted in FORMULA 2, and (e) pharmaceutically acceptable salts thereof.

4. The method according to claim 1, wherein said halogenated fluorescein has either Formulas I or Formula II, below, X is oxygen or nitrogen, "n" is zero or 1 such that when X is Formula I

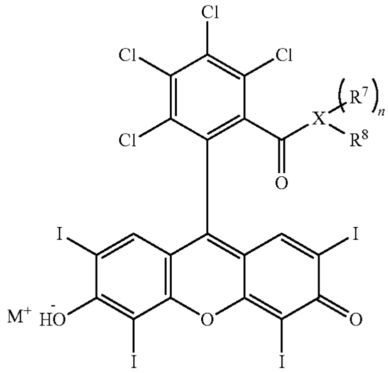

-continued

Formula II

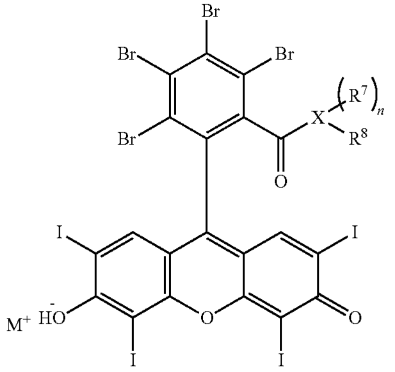

oxygen, n is zero, $R^7$ is absent, and $R^8$ is present as an aromatic ring-containing ester substituent, whereas when X is nitrogen, n is 1 and $R^7$ is present, and —$XR^7R^8$ is an aromatic ring-containing amide substituent;

wherein said aromatic ring-containing substituent is a single ring containing 5- or 6-members, or a 5,6- or 6,6-fused aromatic ring system, in which the single aromatic ring or fused aromatic ring system contains 0, 1 or 2 hetero ring atoms that are independently nitrogen, oxygen or sulfur;

when X is nitrogen, $R^7$ and $R^8$ are the same or different and are selected from the group consisting of hydrogen, $C_1$-$C_4$ alkyl, an aromatic ring-containing substituent or together with amido nitrogen atom $R^7$ and $R^8$ together with amido nitrogen atom form a 5- or 6-membered ring.

5. The method according to claim 4, wherein said aromatic ring-containing substituent of said aromatic ester or aromatic amide unsubstituted, and is selected from the group consisting of the following

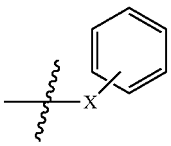, 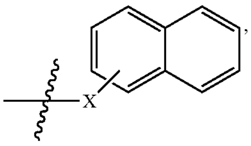,

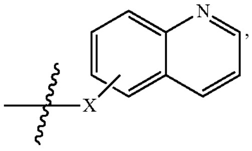, 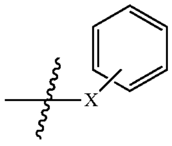,

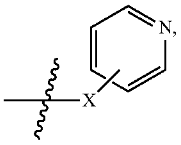, 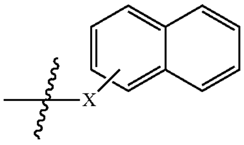,

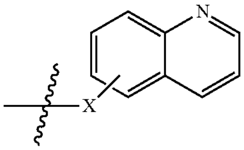, 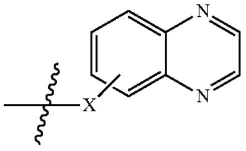,

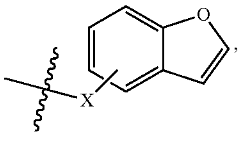, 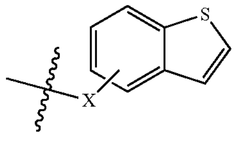 and

-continued

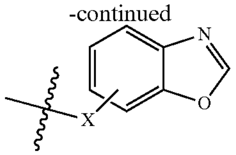

where

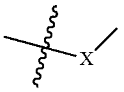

is

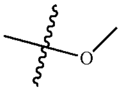 [SMILES: *OC]

or

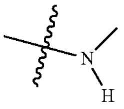 [SMILES: *NC]

providing an ester or the $R^8$ group is hydrogen forming a monosubstituted amide, respectively.

6. The method according to claim 1, wherein said halogenated fluorescein or pharmaceutically acceptable salt or ester has the chemical formula of one or both of Formulas Ia and/or IIb Ia

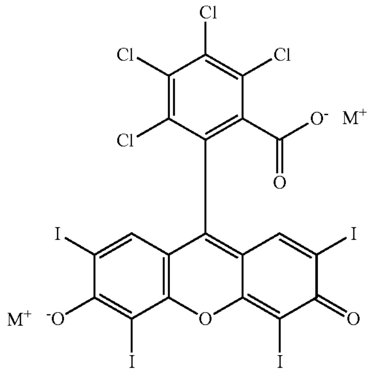

IIb

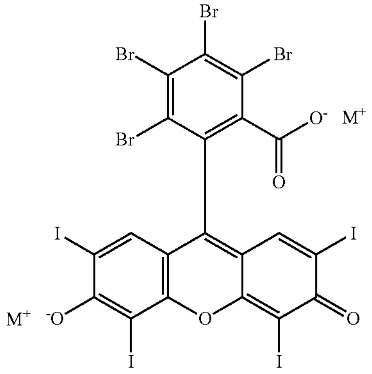

wherein $M^-$ is a pharmaceutically acceptable cation.

7. The method according to claim 1, wherein said halogenated fluorescein or pharmaceutically acceptable salt or ester thereof is rose bengal disodium.

* * * * *